United States Patent
Covey et al.

(10) Patent No.: US 11,497,754 B2
(45) Date of Patent: Nov. 15, 2022

(54) NEUROSTEROIDS AND ENANTIOMERS THEREOF FOR THE PREVENTION AND TREATMENT OF NEURODEGENERATIVE CONDITIONS

(71) Applicants: Douglas Covey, St. Louis, MO (US); Charles Zorumski, St. Louis, MO (US); Yukitoshi Izumi, St. Louis, MO (US); Makoto Ishikawa, St. Louis, MO (US)

(72) Inventors: Douglas Covey, St. Louis, MO (US); Charles Zorumski, St. Louis, MO (US); Yukitoshi Izumi, St. Louis, MO (US); Makoto Ishikawa, St. Louis, MO (US)

(73) Assignee: Washington University, St. Louis, MO (US)

( * ) Notice: Subject to any disclaimer, the term of this patent is extended or adjusted under 35 U.S.C. 154(b) by 174 days.

(21) Appl. No.: 16/782,406

(22) Filed: Feb. 5, 2020

(65) Prior Publication Data

US 2020/0246356 A1     Aug. 6, 2020

Related U.S. Application Data

(60) Provisional application No. 62/801,187, filed on Feb. 5, 2019.

(51) Int. Cl.
*A61P 27/06* (2006.01)
*A61K 31/57* (2006.01)
*A61K 9/00* (2006.01)
*A61K 47/40* (2006.01)

(52) U.S. Cl.
CPC ............ *A61K 31/57* (2013.01); *A61K 9/0019* (2013.01); *A61K 9/0048* (2013.01); *A61K 47/40* (2013.01); *A61P 27/06* (2018.01)

(58) Field of Classification Search
CPC ....................................... A61P 27/06
See application file for complete search history.

(56) References Cited

U.S. PATENT DOCUMENTS

| | | |
|---|---|---|
| 10,202,413 B2 | 2/2019 | Covey |
| 2011/0306579 A1 | 12/2011 | Stein |
| 2013/0090317 A1 | 4/2013 | Vanlandingham et al. |
| 2015/0366953 A1 | 12/2015 | Danias et al. |
| 2016/0184322 A1 | 6/2016 | Vanlandingham et al. |

FOREIGN PATENT DOCUMENTS

WO     2017156103 A1     9/2017

OTHER PUBLICATIONS

The Foundation/American Society of Retina Specialists. "Intravitreal Injections." (2017). Accessed Dec. 16, 2021. (Year: 2017).*
Goldman, David. "Intracameral therapy: The next step in management of ocular disease?" Ophthalmology Web. (Sep. 19, 2008). Accessed Dec. 16, 2021. (Year: 2008).*
"Reconstitution of Solutions." Basicmedicalkey.com. (Feb. 11, 2017). Accessed Dec. 16, 2021. Available from: << https://basicmedicalkey.com/reconstitution-of-solutions/ >>. (Year: 2017).*
Ishikawa, M., et al. "Neurosteroids Are Endogenous Neuroprotectants in an Ex Vivo Glaucoma Model." IOVS. (Dec. 2014), vol. 55, No. 12, pp. 8531-8541. (Year: 2014).*
Hirt et al., "Contribution of autophagy to ocular hypertension and neurodegeneration in the DBA/2J spontaneous glaucomo mouse model", Cell Death Discovery, 2018, vol. 4, No. 75, 13 pages.
Shikawa et al., "Neurosteroids Are Engogenous Neuroprotectants in an Ex Vivo Glaucoma Model", IOVS, Dec. 2014, vol. 55, No. 12, pp. 8531-8541.
Ishikawa et al., "Additive neuroprotective effects of 24(S)-hydroxycholesterol and allopregnanolone in an ex vivo rate glaucoma model", Scientific Reports, 2018, vol. 8, No. 12851, pp. 1-15.

* cited by examiner

*Primary Examiner* — John S Kenyon
(74) *Attorney, Agent, or Firm* — Armstrong Teasdale LLP

(57) ABSTRACT

The present disclosure is directed to a composition for prevention or treatment of neurodegenerative conditions. The composition comprises a neurosteroid, a synthetic enantiomer of a neurosteroid, or a combination thereof.

10 Claims, 25 Drawing Sheets

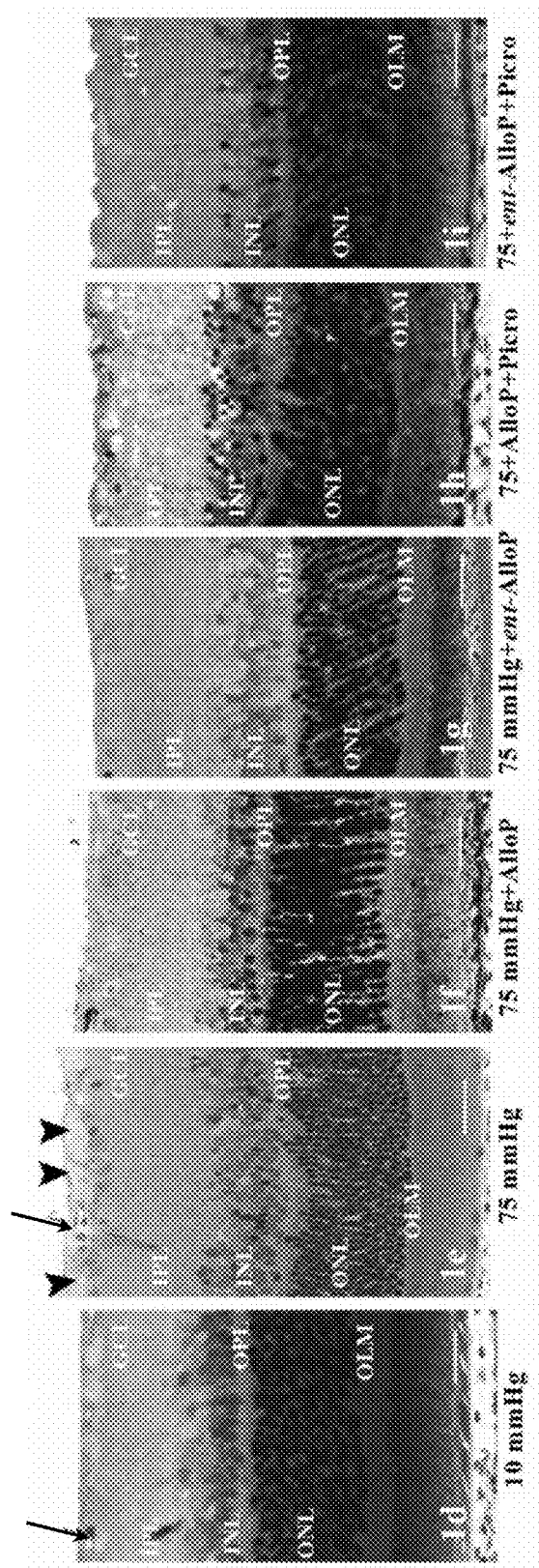

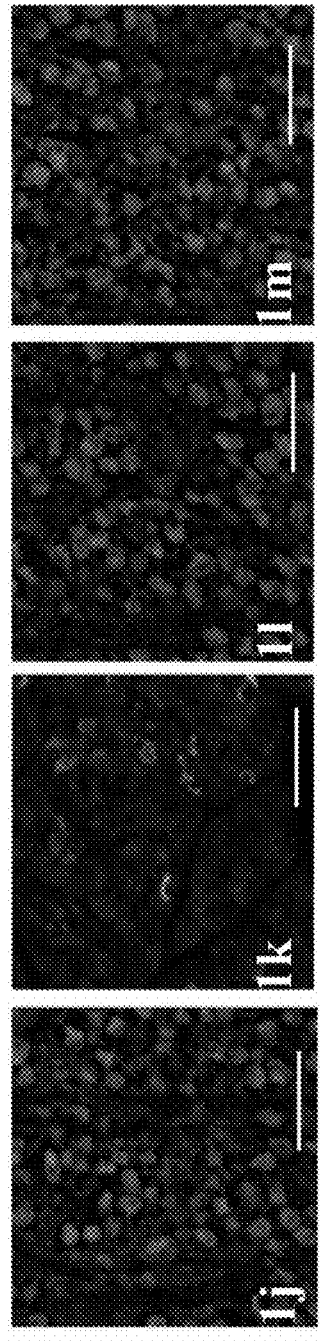
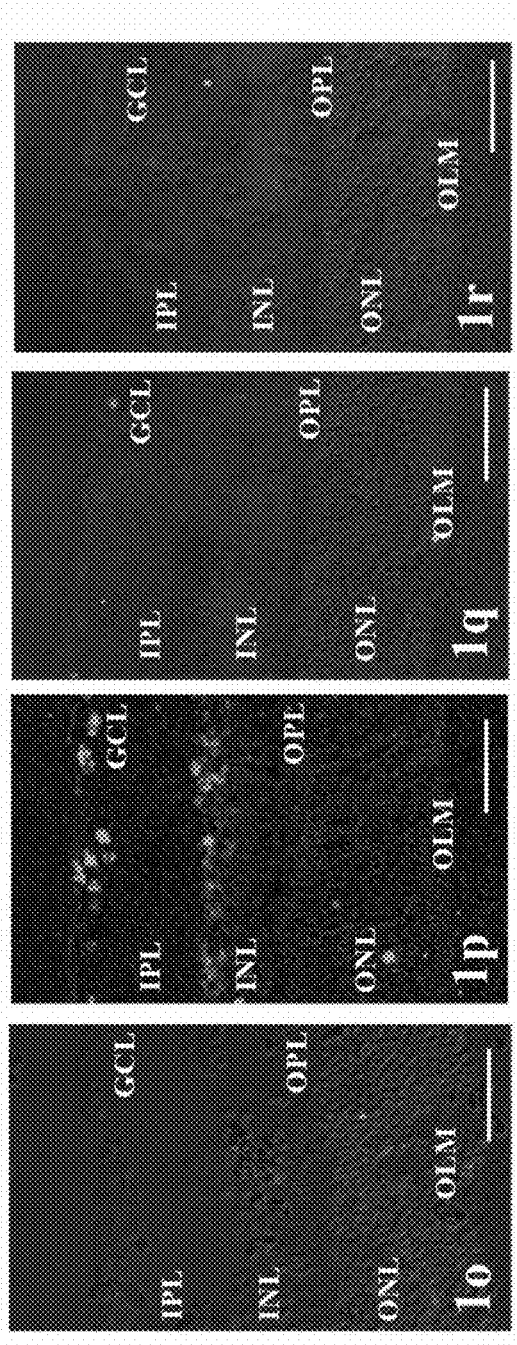

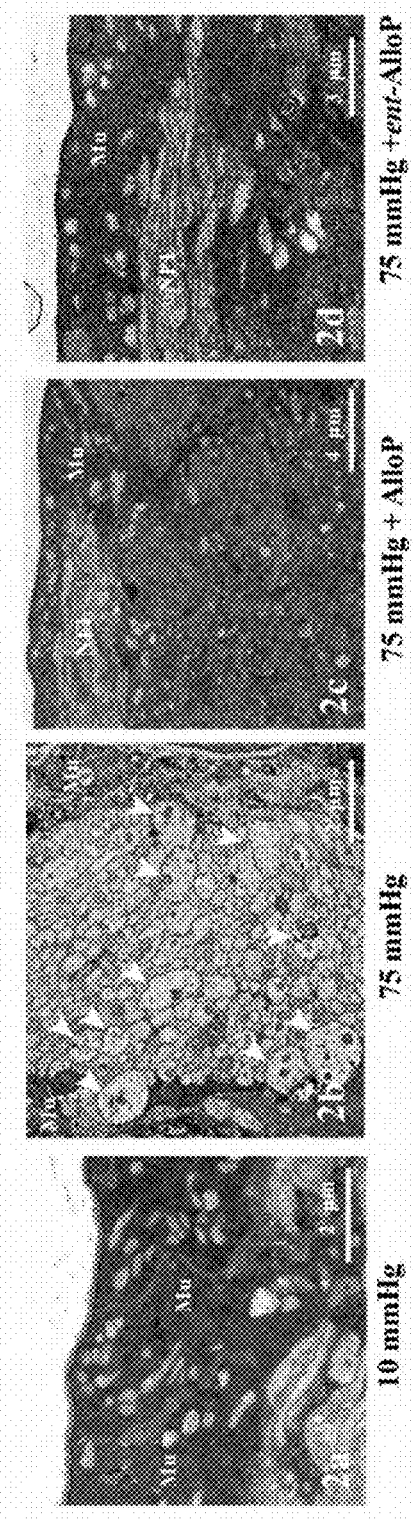

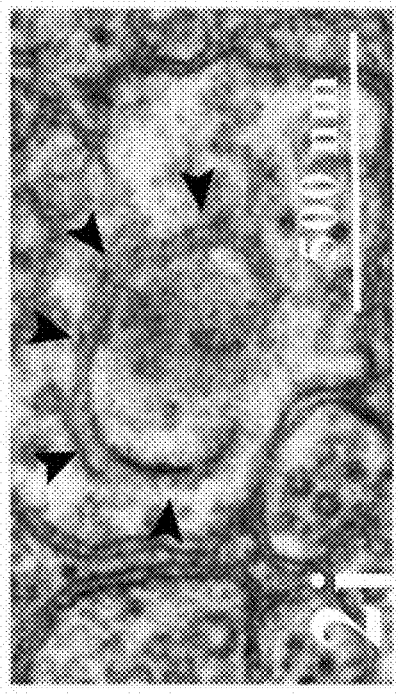
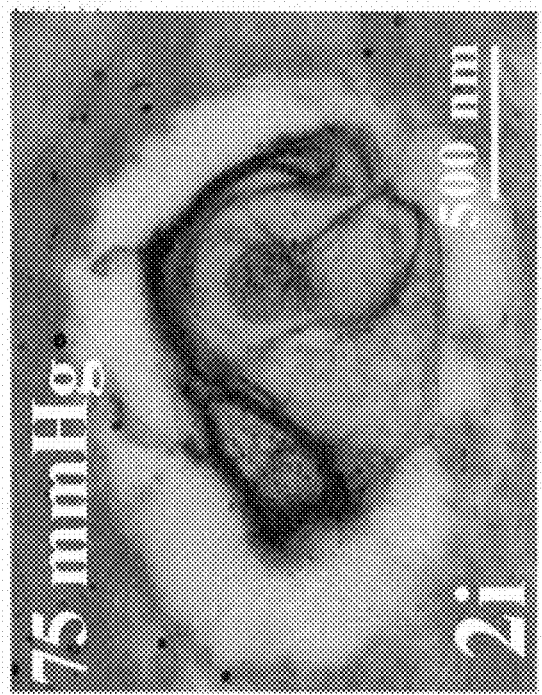
FIG. 2I
FIG. 2J
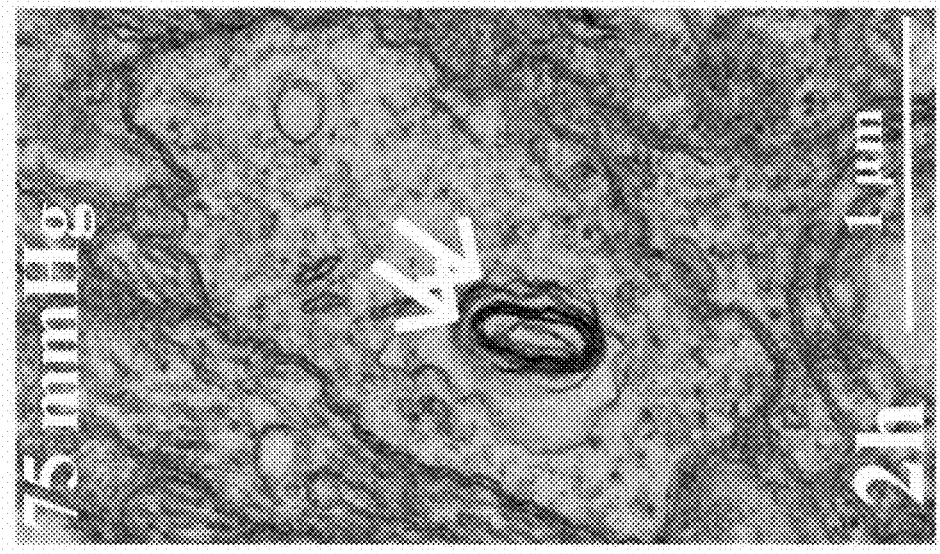
FIG. 2H

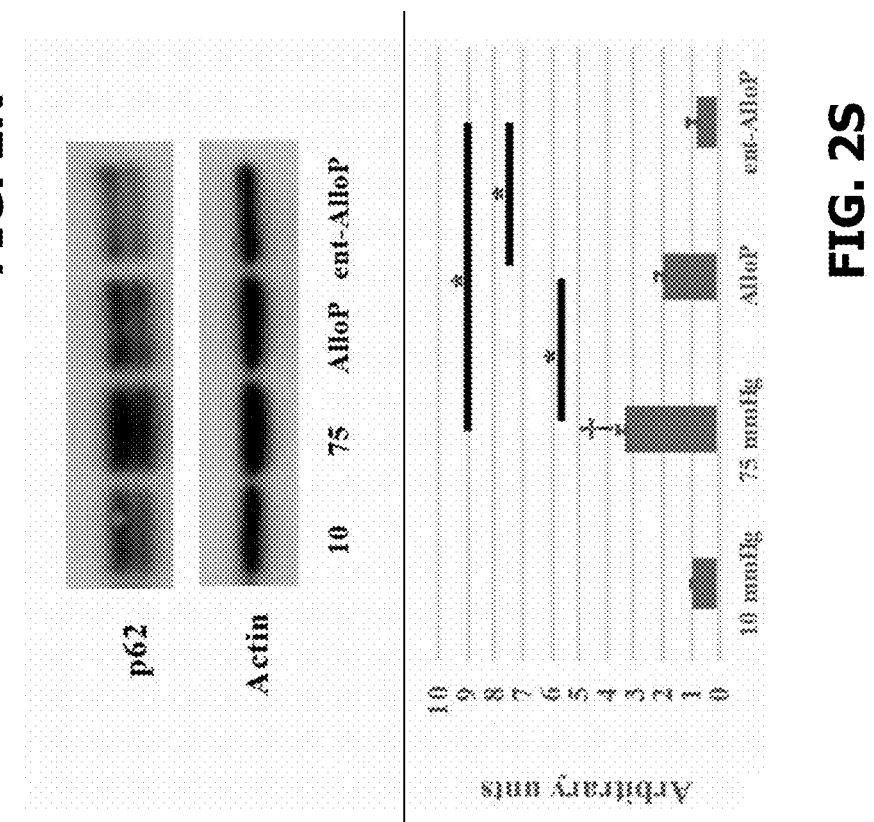
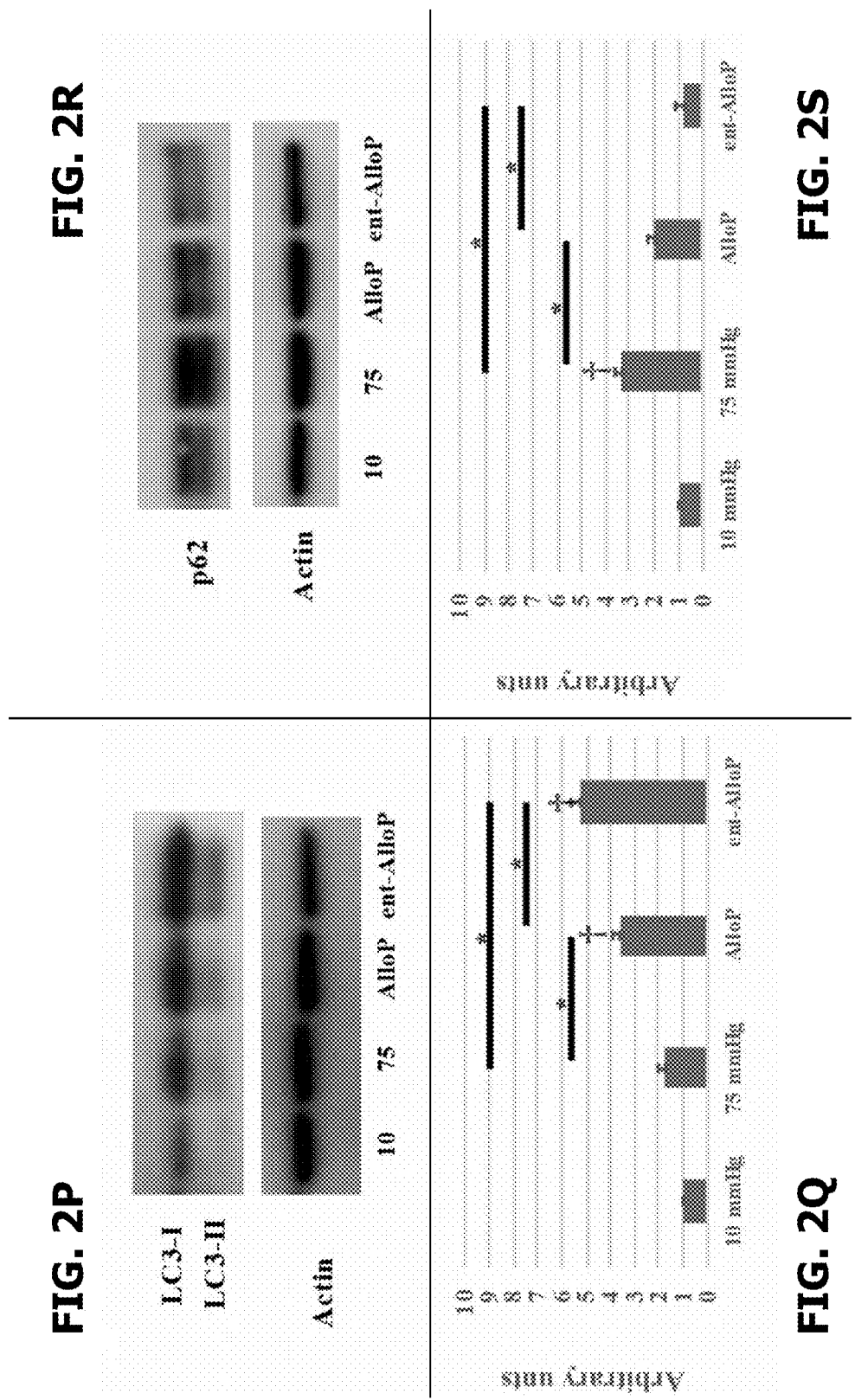
FIG. 2R  FIG. 2S  FIG. 2P  FIG. 2Q

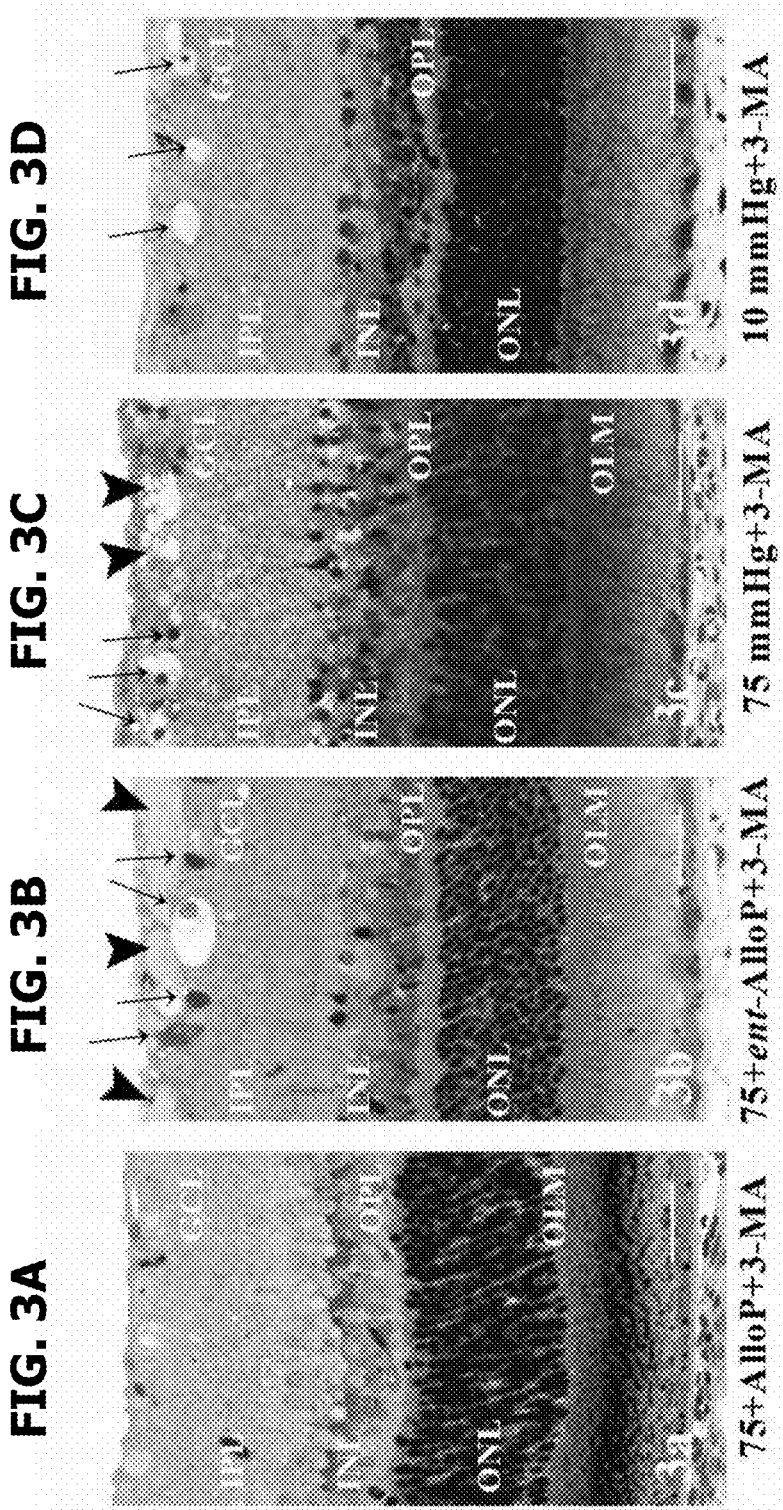

FIG. 4J       FIG. 4K
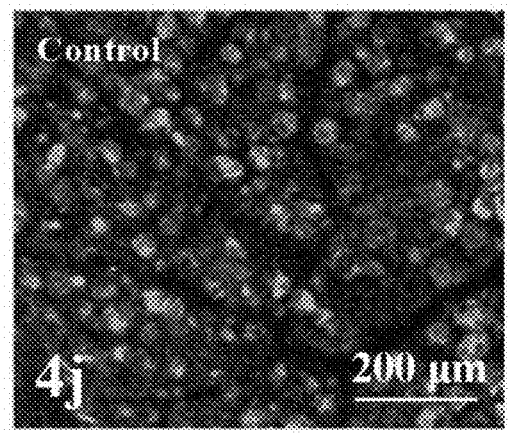
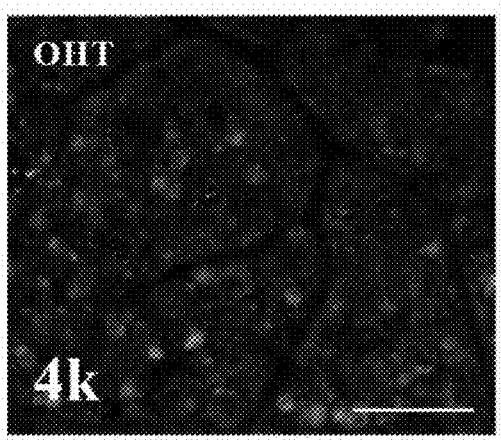
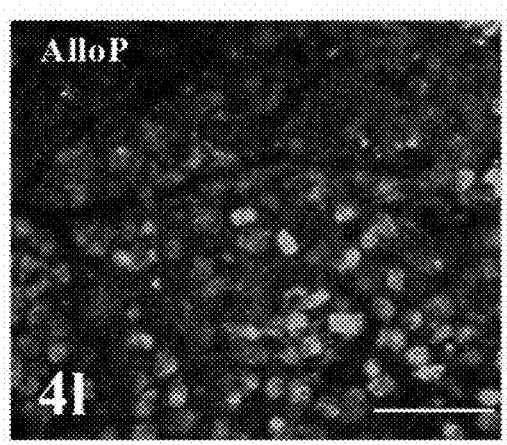
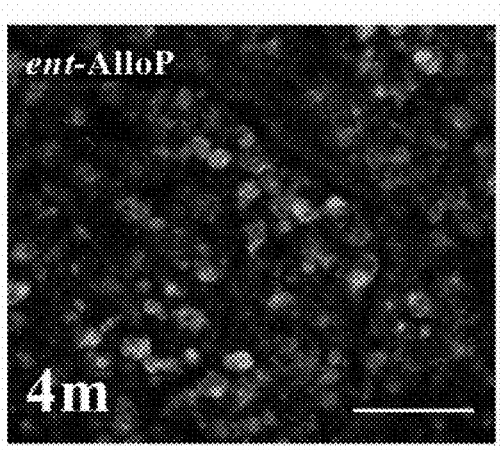
FIG. 4L       FIG. 4M
FIG. 4N
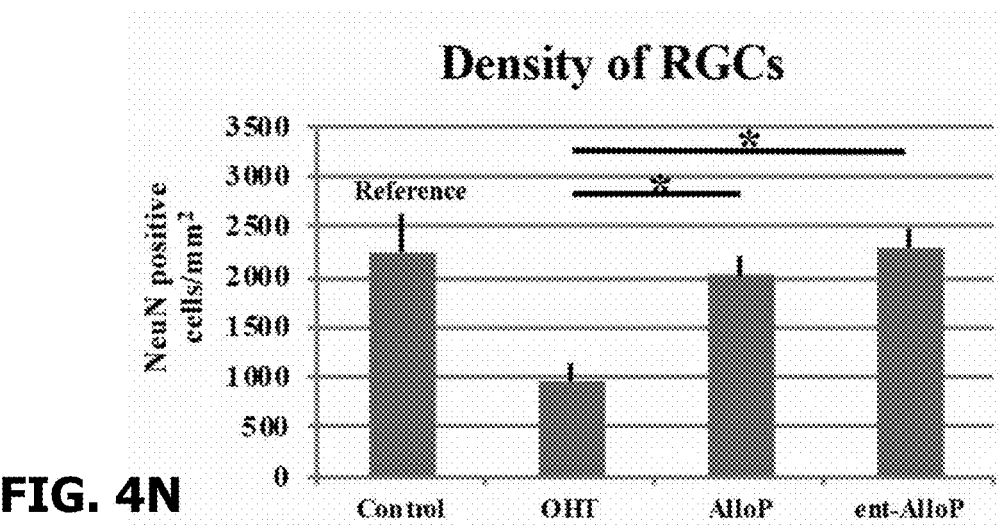

FIG. 5G  FIG. 5H  FIG. 5I
FIG. 5J  FIG. 5K  FIG. 5L
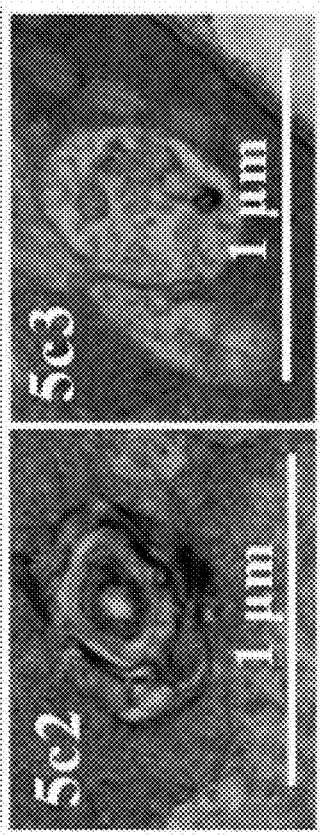

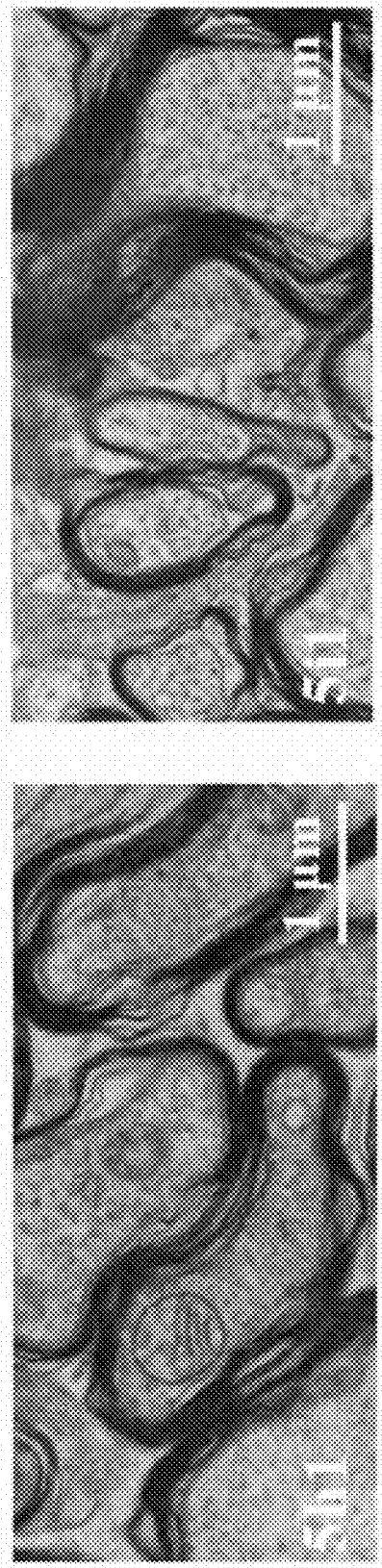
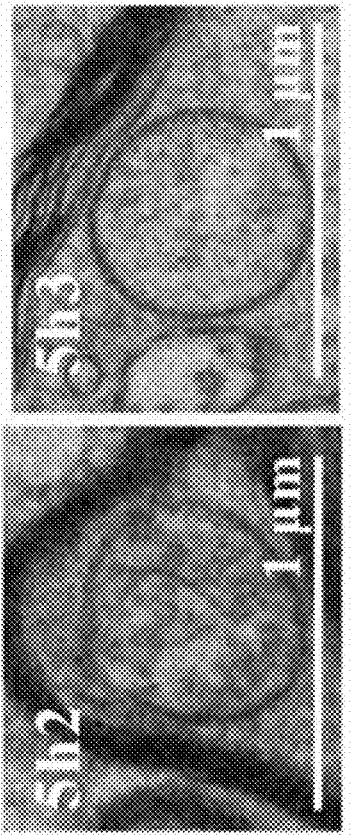
FIG. 5S  FIG. 5T  FIG. 5U  FIG. 5V  FIG. 5W  FIG. 5X

NEUROSTEROIDS AND ENANTIOMERS THEREOF FOR THE PREVENTION AND TREATMENT OF NEURODEGENERATIVE CONDITIONS

CROSS-REFERENCE TO RELATED APPLICATIONS

This application claims priority to U.S. Provisional Application No. 62/801,187, filed Feb. 5, 2019, the content of which is incorporated herein by reference in its entirety.

GOVERNMENT SUPPORT CLAUSE

This invention was made with government support under MH101874 and MH077791 awarded by the National Institutes of Health. The government has certain rights in the invention.

BACKGROUND OF THE DISCLOSURE

Glaucoma is a leading cause of irreversible blindness, and involves selective damage to retinal ganglion cells (RGCs). Increased intraocular pressure (IOP) is a major risk factor for glaucoma. However, the pathogenesis underlying RGC damage by IOP elevation remains unclear.

Autophagy is an intracellular degradation system induced under cellular stress to digest cytoplasmic constituents or cell organelles to maintain nutrient and energy homeostasis. Autophagy begins with an expanding double-membrane structure called a phagophore or isolation membrane in the cytoplasm. The isolation membrane sequestering cytosolic materials and organelles forms a double-membrane vesicle called an autophagosome (AP). APs fuse with the lysosome to degrade their contents, then become degenerative autophagic vacuoles (DAVs) (FIG. 1A). Autophagy also maintains intracellular homeostasis by eliminating damaged cell organelles and misfolded proteins, and plays an important role in neurodegenerative diseases including glaucoma, age-related macular degeneration, retinal vascular occlusion, diabetic retinopathy, Alzheimer's disease and traumatic brain injury.

In general, a neurosteroid is an endogenous or non-endogenous steroid or steroid analogue with the absolute configuration of natural steroids or their unnatural mirror images (enantiomers) that modulate central or peripheral nervous system function. Enantiomers of natural steroids do not occur in nature, accordingly steroid enantiomers are synthetic. Endogenous neurosteroids are modulators generated in the nervous system in response to cellular stress and are potent modulators of neurotransmitter systems. For purposes of this disclosure, the term "neurosteroid" is used to designate any neurosteroid, any neuroactive steroid, any steroid that is made locally in the brain, any steroid not made in the brain but made elsewhere in the body that alters brain function, and any synthetic steroid that alters brain function. Neurosteroids and enantiomeric neurosteroids include, but are not limited to allopregnanolone, cholesterol, pregnenolone, progesterone, pregn-5α-ane-3,17-dione, pregn-5β-ane-3,17-dione, androsterone, etiocholanolone, tetrahydrodeoxycorticosterone, and any of the neurosteroids disclosed in U.S. Pat. No. 10,202,413 B2, which is herein incorporated by reference.

Among them, allopregnanolone (AlloP) is a strong enhancer of $GABA_A$ receptors. AlloP attenuates pressure-induced retinal injury in ex vivo rat retinas. Because neuroprotective effects of AlloP were inhibited by a specific $GABA_A$ antagonist, the neuroprotection with AlloP is likely mediated by GABAergic signaling. However, neuroprotection by AlloP may not exclusively involve $GABA_A$ receptors. AlloP was found to activate autophagy in a mouse model of Niemann-Pick Type C disease and in primary astrocyte cultures, suggesting that upregulation of autophagic flux may contribute to endogenous neuroprotective mechanisms. Ent-AlloP is the synthetic enantiomer of AlloP (FIG. 1B) and has weak actions on $GABA_A$ receptor signaling. In spite of its differences from AlloP, ent-AlloP may have neuroprotective effects in a mouse model of Niemann-Pick Type C disease, raising the possibility that ent-AlloP acts via mechanisms distinct from AlloP.

As described herein, a rat ex vivo ocular hypertension (OHT) model with a closed chamber incubation system (FIG. 1C) and an in vivo OHT model following injection of polystyrene microbeads into the anterior chamber were used to compare neuroprotective effects of AlloP and ent-AlloP, focusing on the role of $GABA_A$ receptors and autophagy.

BRIEF DESCRIPTION OF THE DISCLOSURE

In one aspect, the present disclosure is directed to a composition for prevention or treatment of a neurodegenerative condition. The composition comprises a neurosteroid, a synthetic enantiomer of a neurosteroid, or a combination thereof.

In another aspect, the present disclosure is directed to a method of preventing or treating a neurodegenerative condition comprising inducing autophagy. The method comprises administering an effective amount of a composition comprising a neurosteroid, a synthetic enantiomer of a neurosteroid, or a combination thereof.

In yet another, aspect, the present disclosure is directed to a method of attenuating pressure-induced retinal injury. The method comprises administering an effective amount of a composition comprising a neurosteroid, a synthetic enantiomer of a neurosteroid, or a combination thereof.

BRIEF DESCRIPTION OF THE DRAWINGS

The embodiments described herein may be better understood by referring to the following description in conjunction with the accompanying drawings.

FIGS. 1(A-S) are exemplary embodiments of autophagy flux and neuroprotective effects of neurosteroids on pressure-mediated retinal degeneration in an ex vivo model in accordance with the present disclosure. FIG. 1D discloses a light micrograph of pressure-loaded retina at 10 mmHg (arrow indicates blood capillary). FIG. 1E discloses a light micrograph of pressure-loaded retina at 75 mmHg (arrowheads indicate axonal swelling). FIG. 1F discloses a light micrograph of pressure-loaded retina at 75 mmHg with 1 µM AlloP. FIG. 1G discloses a light micrograph of pressure-loaded retina at 75 mmHg with 1 µM ent-AlloP. FIG. 1H discloses a light micrograph of pressure-loaded retina with administration of 1 µM AlloP and 1 µM picrotoxin. FIG. 1I discloses a light micrograph of pressure-loaded retina with administration of 1 µM ent-AlloP and 1 µM picrotoxin, scale bars 20 mm. FIG. 1J discloses RGC survival and neuroprotection in pressure-loaded whole mounted retinas at 10 mmHg. FIG. 1K discloses RGC survival and neuroprotection in pressure-loaded whole mounted retinas at 75 mmHg. FIG. 1L discloses RGC survival and neuroprotection in pressure-loaded whole mounted retinas with 1 μM AlloP at 75 mmHg. FIG. 1M discloses RGC survival and neuroprotection in pressure-loaded whole mounted retinas with 1 μM ent-AlloP at 75 mmHg, scale bars 200 μm. FIG. 1O discloses 10 mmHg TUNEL staining. FIG. 1P discloses 75 mmHg TUNEL staining. FIG. 1Q discloses TUNEL staining with 1 μM AlloP. FIG. 1R discloses TUNEL staining with 1 μM ent-AlloP, scale bars 30 μm.

FIGS. 2(A-S) are exemplary embodiments of electron micrographic and Western blot analyses of ex vivo retinas in accordance with the present disclosure. FIG. 2A discloses an electron micrographic of an ex vivo retina at 10 mmHg ("Mu" indicates Müller cell). FIG. 2B discloses an electron micrographic of an ex vivo retina at 75 mmHg (arrowheads indicate swollen axons). FIG. 2C discloses an electron micrographic of an ex vivo retina with AlloP (1 μM) at 75 mmHg ("NFL" indicates nerve fiber layer). FIG. 2D discloses an electron micrographic of an ex vivo retina with ent-AlloP (1 μM) at 75 mmHg. FIG. 2H discloses a DAV (indicated by double arrows) in the NFL at 75 mmHg. FIG. 2I discloses a DAV in the NFL at 75 mmHg. FIG. 2J discloses an isolation membrane in the NFL at 75 mmHg. FIG. 2P discloses representative Western blot analyses of LC3. FIG. 2Q discloses quantitative Western blot analysis of LC3II expression (Dunnett †p<0.05 or Tukey *p<0.05). FIG. 2R discloses representative Western blot analyses of p62. *p<0.05. FIG. 2S discloses quantitative Western blot analysis of p62 expression (Dunnett †p<0.05 or Tukey *p<0.05).

FIGS. 3(A-H) are exemplary embodiments of effects of pressure elevation, neurosteroids, and 3-MA in accordance with the present disclosure. FIG. 3A discloses a light micrograph of retinal morphology for administration of 10 mM 3-MA with no differences in the retina incubated with 1 μM AlloP at 75 mmHg. FIG. 3B discloses a light micrograph of retinal morphology for administration of 10 mM 3-MA with dampened protective effects of 1 μM ent-AlloP at 75 mmHg (arrowheads indicate axonal swelling; arrows indicate RGC degeneration). FIG. 3C discloses a light micrograph of retinal morphology with severe induced damage by 3-MA (10 mM) at 75 mmHg. FIG. 3D discloses a light micrograph of retinal morphology with induced degeneration by 3-MA (10 mM) at 10 mmHg, scale bars, 20 μm.

FIGS. 4(A-S) are exemplary embodiments of effects of IOP and neurosteroids on RGC or axonal survival in accordance with the present disclosure. FIG. 4J discloses a confocal image of NeuNlabeled RGCs in a Control eye. FIG. 4K discloses a confocal image of NeuNlabeled RGCs in a microbead-injected OHT eye without neurosteroid administration. FIG. 4L discloses a confocal image of NeuNlabeled RGCs with administration of 1 μM AlloP or FIG. 4M discloses a confocal image of NeuNlabeled RGCs with administration of 1 μM ent-AlloP, scale bars 200 μm. FIG. 4N discloses the number of NeuN-positive cells in the whole mount retina under each condition (Tukey *p<0.05). FIG. 4O discloses a light micrograph of the optic nerve axons three weeks after microbead injection for a control eye. FIG. 4P discloses a light micrograph of the optic nerve axons three weeks after microbead injection for microbead-injected eyes with OHT. FIG. 4Q discloses a light micrograph of the optic nerve axons three weeks after microbead injection with administration of 1 μM AlloP. FIG. 4R discloses a light micrograph of the optic nerve axons three weeks after microbead injection with administration of 1 μM ent-AlloP, scale bars 10 μm.

FIGS. 6(A-D) are exemplary embodiments of Western blotting in in vivo OHT eyes in accordance with the present disclosure.

DETAILED DESCRIPTION OF THE DISCLOSURE

Figure 1A:
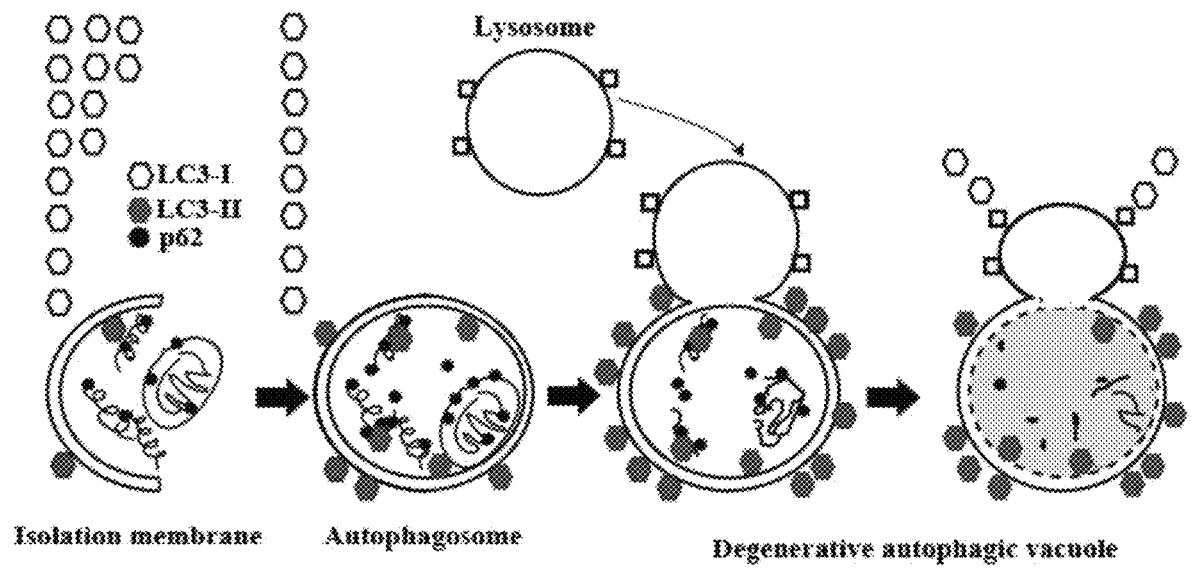
FIG. 1A discloses key steps of autophagy flux.
Figure 1B:
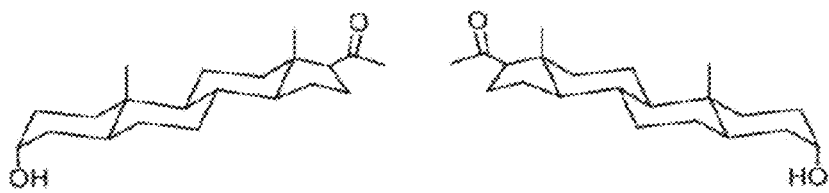
FIG. 1B discloses structures of neurosteroids.

It is described herein that the neurosteroid, allopregnanolone (AlloP), and its enantiomer (ent-AlloP) are similarly neuroprotective in both in vivo and ex vivo rat models of glaucoma. In the ex vivo model, ent-AlloP was neuroprotective via autophagy activation but, unlike AlloP, not via $GABA_A$ receptor modulation. Immunoblotting analysis revealed that AlloP increased LC3-II and decreased p62. Electron microscopic analysis showed that AlloP increased autophagosomes (APs) without altering numbers of degenerative autophagic vacuoles (DAVs). ent-AlloP markedly increased DAVs and LC3-II without altering APs but suppressing p62 levels more effectively, indicating that autophagy activation is a major mechanism underlying its neuroprotective effects.

Thus, AlloP and ent-AlloP serve as potential therapeutic agents for treatment of glaucoma but these enantiomers protect the retina by distinct mechanisms. Therapeutic agents include compositions comprising at least one of a neurosteroid and a synthetic enantiomer of the neurosteroid, such that an administered effective amount of the composition is a therapeutically effective amount. The exact amount of a compound required to achieve an effective amount will vary from subject to subject, depending, for example, on age, general condition of a subject, identity of the particular compound(s), mode of administration, and the like. The compounds or neurosteroids of the present disclosure are useful for at least inducing autophagy, attenuating pressure-induced retinal injury, and other benefits described herein in a subject, e.g., a human subject, and are preferably administered in the form of an effective amount of a compound (or combination of compounds) of the instant disclosure and optionally or additional components.

In some embodiments, the present disclosure is directed to a composition for prevention or treatment of a neurodegenerative condition comprising a neurosteroid, a synthetic enantiomer of a neurosteroid, or a combination thereof. In some embodiments, the composition comprises a neurosteroid. In some embodiments, the composition comprises a synthetic enantiomer of a neurosteroid. In some embodiments, the composition comprises a neurosteroid and a synthetic enantiomer of a neurosteroid.

In some embodiments, the composition further comprises a saline solution. Saline solutions are typically of physiological concentration akin to extracellular fluid in the brain. In some embodiments, the composition further comprises (2-Hydroxypropyl)-β-cyclodextrin (2HBCD). 2HBCD concentration in the composition is from about 1 millimolar to about 10 millimolar, or about 20% (w/v).

In some embodiments, the neurosteroid is allopregnanolone and the synthetic enantiomer of the neurosteroid is ent-allopregnanolone. In some embodiments, the neurosteroid and enantiomeric neurosteroid includes, but are not limited to, allopregnanolone, cholesterol, pregnenolone, progesterone, pregn-5α-ane-3,17-dione, pregn-5β-ane-3,17-dione, androsterone, etiocholanolone, tetrahydrodeoxycorticosterone, and any of the neurosteroids disclosed in U.S. Pat. No. 10,202,413 B2, which is herein incorporated by reference.

In some embodiments the neurosteroid, the synthetic enantiomer of the neurosteroid, or the combination thereof has a concentration of from about 10 nM to about 100 μM.

In some embodiments, the composition comprises the neurosteroid, and a concentration of the neurosteroid is from about 10 nM to about 100 M, from about 100 nM to about 10 M, or about 1 μM.

In some embodiments, the composition comprises the synthetic enantiomer of the neurosteroid, and a concentration of the synthetic enantiomer is from about 10 nM to about 100 μM, from about 100 nM to about 10 μM, or about 1 μM.

In some embodiments, the composition comprises both the neurosteroid and the synthetic enantiomer of the neurosteroid, and a concentration of the combination thereof is from about 10 nM to about 100 μM, from about 100 nM to about 10 M, or about 1 μM.

In some embodiments, the present disclosure is directed to a method of preventing or treating a neurodegenerative condition comprising inducing autophagy by administering an effective amount of the composition. In some embodiments, the present disclosure is directed to a method of attenuating pressure-induced retinal injury, the method comprising administering an effective amount of the composition.

In some embodiments, the neurodegenerative condition is selected from glaucoma, age-related macular degeneration, retinal vascular occlusion, diabetic retinopathy, Alzheimer's disease and traumatic brain injury. In some embodiments, the neurodegenerative condition is glaucoma.

In some embodiments, administering an effective amount of the composition comprises administering the composition by intravitreal injection. In some embodiments, administering an effective amount of the composition comprises administering the composition by intracameral injection.

EXAMPLES

Example 1. Effects of ent-AlloP on Pressure-Mediated Retinal Degeneration in an Ex Vivo Model Retinas incubated at 10 mmHg (FIG. 1D) exhibited normal appearance but those at 75 mmHg showed axonal swelling in the nerve fiber layer (NFL) (FIG. 1E); this damage is attenuated by 1 μM AlloP (FIG. 1F). Surprisingly, it was also found that 1 μM ent-AlloP substantially inhibited axonal swelling (FIG. 1G). To determine whether the neuroprotective effects of AlloP and ent-AlloP involve $GABA_A$ receptors, 1 μM picrotoxin, a $GABA_A$ receptor antagonist, was administered. Picrotoxin overcame the neuroprotective effect of AlloP under hyperbaric conditions (FIG. 1H). However, picrotoxin did not alter the effects of ent-AlloP (FIG. 1I), indicating that the mechanism underlying its neuroprotection is distinct from $GABA_A$ receptor activation Table 1 (see also Table 2).

TABLE 1

Effects of AlloP and ent-AlloP on the NFLT, NDS, and density of damaged cells in the GCL.

| Condition | NFLT vs. RT (%) [p value vs. 75 mmHg] | NDS [p] | Damaged cells in GCL [p] |
|---|---|---|---|
| 10 mmHg | 1.5 ± 0.7 [—] | 0.2 ± 0.4 [—] | 1.9 ± 1.8 [—] |
| 75 mmHg | 11.4 ± 1.9 [—] | 0.9 ± 0.3 [—] | 8.8 ± 2.2 [—] |

TABLE 1-continued

Effects of AlloP and ent-AlloP on the NFLT, NDS, and density of damaged cells in the GCL.

| Condition | NFLT vs. RT (%) [p value vs. 75 mmHg] | NDS [p] | Damaged cells in GCL [p] |
|---|---|---|---|
| 75 mmHg + 1 μM AlloP | 1.5 ± 0.6 [*p < 0.05] | 0.2 ± 0.4 [p > 0.05] | 2.0 ± 1.7 [*p < 0.05] |
| 75 mmHg + 1 μM ent-AlloP | 1.6 ± 0.6 [*p < 0.05] | 0.2 ± 0.4 [p > 0.05] | 1.9 ± 1.2 [*p < 0.05] |
| 75 mmHg + 1 μM AlloP + 1 μM Picro | 4.0 ± 2.6 [*p < 0.05] | 3.1 ± 0.8 [*p < 0.05] | 23.9 ± 6.6 [*p < 0.05] |
| 75 mmHg + 1 μM ent-AlloP + 1 μM Picro | 1.5 ± 0.6 [*p < 0.05] | 0.3 ± 0.5 [p > 0.05] | 2.1 ± 1.1 [*p < 0.05] |
| 75 mmHg + 1 μM ent-AlloP + 10 mM 3-MA | 11.6 ± 0.8 [p > 0.05] | 1.4 ± 0.5 [*p < 0.05] | 17.1 ± 6.0 [p > 0.05] |

Data are mean ± SD. NFLT vs. retinal thickness (RT) (%) refers to the NFLT percentage of total RT. The density of damaged cells in the GCL was counted per 250 μm of retina. P values in each parameter were calculated by Dunnett's test.

TABLE 2

Morphological changes of retinas after pressure-loading and neurosteroids treatment.

| | 10 mmHg | 75 mmHg | 75 mmHg + 1 μM AlloP | 75 mmHg + 1 μM ent-AlloP | 75 mmHg + 1 μM AlloP + 1 μM Picrotoxin | 75 mmHg + 1 μM ent-AlloP + 1 μM Picrotoxin | 75 mmHg + 1 μM ent-AlloP + 3-MA |
|---|---|---|---|---|---|---|---|
| NFLT | | | | | | | |
| 1 | 2.2 | 12.3 | 1.0 | 2.3 | 2.3 | 2.0 | 12.3 |
| 2 | 2.4 | 11.7 | 2.0 | 1.9 | 5.9 | 1.9 | 11.9 |
| 3 | 0.6 | 13.1 | 0.9 | 1.0 | 1.2 | 1.8 | 11.0 |
| 4 | 0.5 | 9.3 | 2.0 | 1.5 | 3.4 | 2.5 | 11.2 |
| 5 | 1.3 | 12.2 | 1.3 | 1.8 | 5.1 | 0.8 | 11 |
| 6 | 1.8 | 13.4 | 0.9 | 0.7 | 1.9 | 0.7 | 10.5 |
| 7 | 1.5 | 8.1 | 2.2 | 1.9 | 8.9 | 1.5 | 11.9 |
| 8 | 2 | 12.9 | 2.3 | 2.5 | 5.3 | 1.7 | 12.9 |
| 9 | 0.8 | 10.0 | 0.8 | 1.0 | 2.1 | 1.0 | 11.3 |
| Average | 1.5 | 11.4 | 1.5 | 1.6 | 4.0 | 1.5 | 11.6 |
| SD | 0.7 | 1.9 | 0.6 | 0.6 | 2.6 | 0.6 | 0.8 |
| Dunnett's test | | vs | <0.05* | <0.05* | <0.05* | <0.05* | >0.05 |
| NDS | | | | | | | |
| 1 | 0 | 1 | 1 | 0 | 4 | 0 | 1 |
| 2 | 1 | 1 | 0 | 1 | 3 | 0 | 2 |
| 3 | 0 | 0 | 0 | 0 | 2 | 0 | 1 |
| 4 | 0 | 1 | 0 | 1 | 4 | 1 | 1 |
| 5 | 0 | 1 | 0 | 0 | 4 | 0 | 1 |
| 6 | 1 | 1 | 0 | 0 | 3 | 1 | 2 |
| 7 | 0 | 0 | 1 | 0 | 3 | 0 | 2 |
| 8 | 0 | 1 | 0 | 0 | 2 | 1 | 1 |
| 9 | 0 | 1 | 0 | 0 | 3 | 0 | 2 |
| Average | 0.2 | 0.8 | 0.2 | 0.2 | 3.1 | 0.3 | 1.4 |
| SD | 0.4 | 0.4 | 0.4 | 0.4 | 0.8 | 0.5 | 0.5 |
| Dunnett's test | | vs | >0.05 | >0.05 | <0.05* | >0.05 | <0.05* |
| Damaged cell | | | | | | | |
| 1 | 0 | 17 | 2 | 1 | 21 | 1 | 25 |
| 2 | 4 | 21 | 4 | 1 | 14 | 3 | 14 |
| 3 | 0 | 15 | 3 | 4 | 30 | 2 | 14 |
| 4 | 2 | 10 | 0 | 2 | 21 | 1 | 12 |
| 5 | 3 | 25 | 0 | 1 | 34 | 1 | 13 |
| 6 | 2 | 15 | 1 | 3 | 21 | 2 | 13 |
| 7 | 1 | 15 | 5 | 1 | 25 | 2 | 23 |
| 8 | 5 | 23 | 2 | 3 | 31 | 4 | 13 |
| 9 | 0 | 12 | 1 | 1 | 18 | 3 | 27 |
| Average | 1.9 | 17.0 | 2.0 | 1.9 | 23.9 | 2.1 | 17.1 |
| SD | 1.8 | 5.0 | 1.7 | 1.2 | 6.6 | 1.1 | 6.0 |
| Dunnett's test | | vs | <0.05* | <0.05* | <0.05* | <0.05* | >0.05 |

Example 2. ent-AlloP Preserves Neuronal Nuclear Antigen Under High Pressure

In whole mounted retinas, RGC damage induced by pressure elevation was visualized as a reduction in cells positive for NeuN. FIG. 1J illustrates examples of confocal images of NeuN-labeled RGCs that were obtained from a control eye incubated at 10 mmHg. Pressure elevation (75 mmHg) reduced the number of cells positive for NeuN (FIG. 1K). The confocal images in FIG. 1L and FIG. 1M illustrate the neuroprotective effects of AlloP (1 µM) and ent-AlloP (1 µM) on RGC survival in hyperbaric conditions, respectively. The preservation of RGC by ent-AlloP is as efficient as AlloP. The graph in FIG. 1N discloses the number of NeuN positive RGCs in the retina in each condition (Table 3).

TABLE 3

Figure 1C:
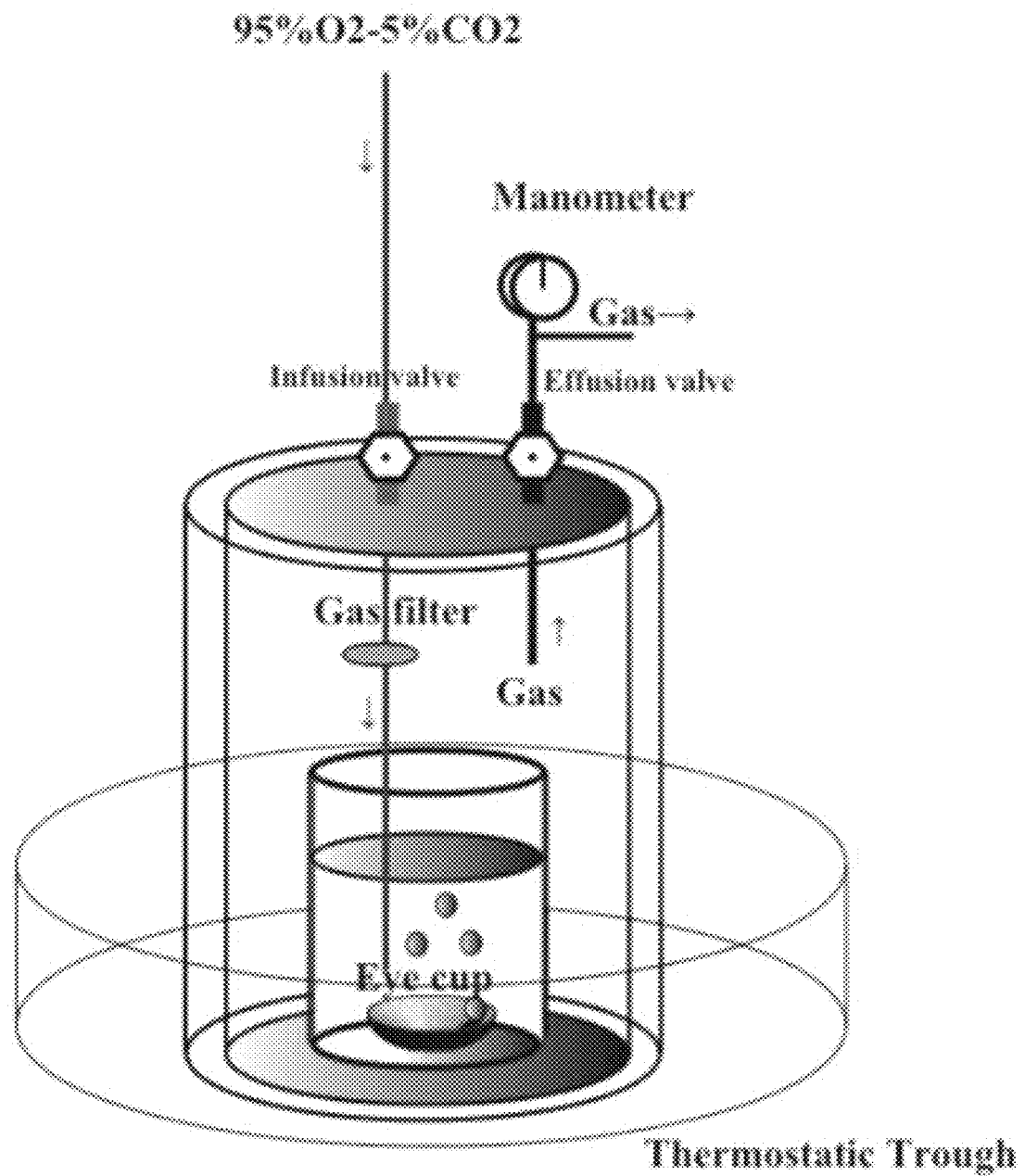
FIG. 1C discloses a closed pressure-loading system.
Figure 1N:
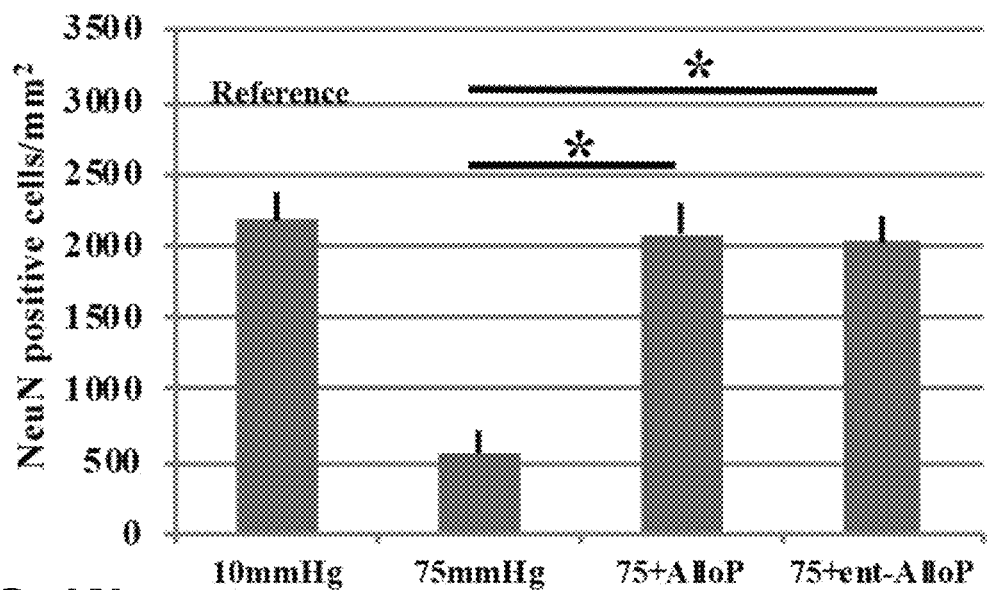
FIG. 1N discloses the number of NeuN-positive cells in whole mount retinas (Tukey *p<0.05).

RGC Survival (FIG. 1N)

| | 10 mmHg | 75 mmHg | 75 mmHg + AlloP | 75 mmHg + ent-AlloP |
|---|---|---|---|---|
| 1 | 2500 | 480 | 2240 | 2280 |
| 2 | 2060 | 840 | 1860 | 2000 |
| 3 | 1980 | 460 | 2260 | 1840 |
| 4 | 2180 | 540 | 1840 | 1860 |
| 5 | 2160 | 480 | 2220 | 2120 |
| Average | 2176 | 560.0 | 2084.0 | 2020.0 |
| SD | 198.2 | 159.4 | 214.2 | 184.4 |
| Dunnett | vs | | <0.05* | <0.05* |
| Tukey | vs | | <0.05* | <0.05* |
| | | | vs | >0.05 |

Example 3. ent-ADoP Prevents Pressure-Induced Apoptosis

At 10 mmHg, a few TUNEL-positive cells are observed in the ganglion cell layer (GCL) and outer nuclear layer (ONL) (FIG. 1O). Exposure to elevated pressure (75 mmHg) induced apoptosis that was apparent in the GCL and the inner nuclear layer (INL) (FIG. 1P). The number of TUNEL-positive cells was reduced by AlloP (FIG. 1Q). Similar protection was observed with ent-AlloP (FIG. 1R). TUNEL staining with 1 µM AlloP (FIG. 1Q) or 1 µM ent-AlloP (FIG. 1R) showed significant decrease in the number of TUNEL-positive cells at 75 mmHg. The graph in FIG. 1S discloses the number of apoptotic cells in the retina in each condition (Table 4).

TABLE 4

Figure 1S:
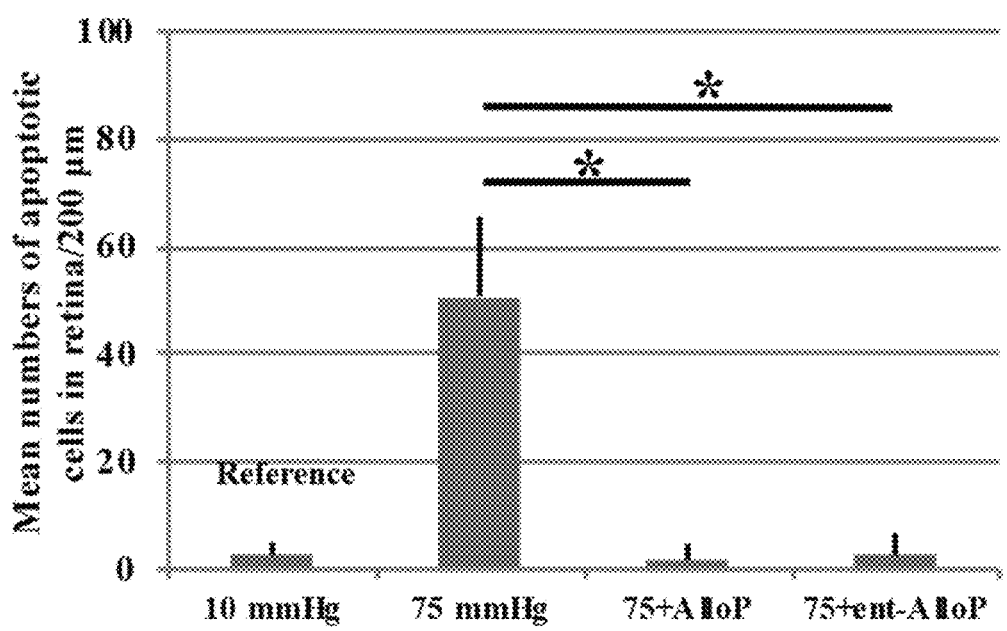
FIG. 1S discloses the number of TUNEL-positive RGCs per 200 Lm of retina section (Tukey *p<0.05).

TUNEL Staining (FIG. 1S)

| | 10 mmHg | 75 mmHg | 75 mmHg + AlloP | 75 mmHg + ent-AlloP |
|---|---|---|---|---|
| 1 | 3 | 62 | 0 | 1 |
| 2 | 3 | 60 | 0 | 0 |
| 3 | 0 | 57 | 0 | 0 |
| 4 | 6 | 26 | 2 | 2 |
| 5 | 2 | 49 | 7 | 10 |
| Average | 2.8 | 50.8 | 1.8 | 2.6 |
| SD | 2.2 | 14.7 | 3.0 | 4.2 |
| Dunnett | vs | | <0.05* | <0.05* |
| Tukey | vs | | <0.05* | <0.05* |
| | | | vs | >0.05 |

Figures 2E, 2F, 2G:
FIG. 2E discloses a DAV (indicated by double arrows) in the NFL at 10 mmHg.
FIG. 2F discloses AP in the NFL at 10 mmHg.
FIG. 2G discloses a DAV in the NFL at 10 mmHg.
Figure 2M:
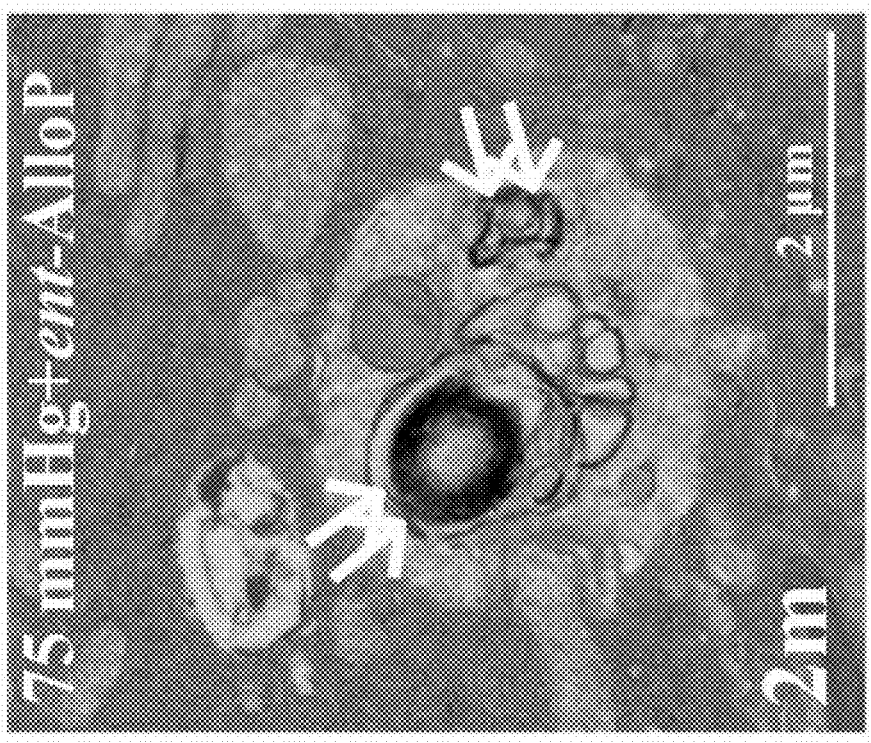
FIG. 2M discloses 1 μM ent-AlloP at 75 mmHg with DAV indicated by double arrows.
Figure 2K:
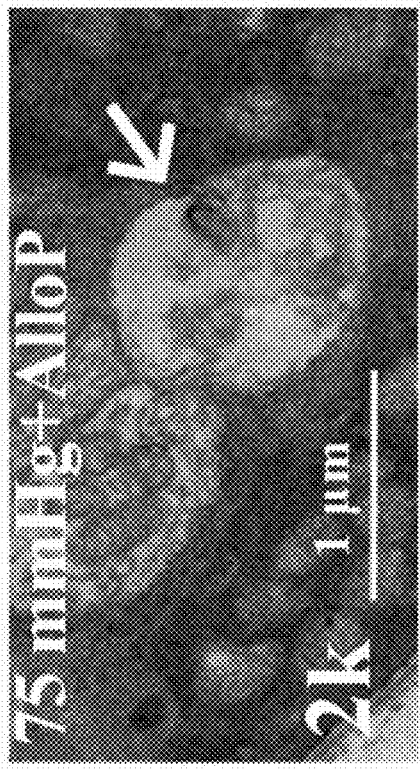
FIG. 2K discloses 1 μM AlloP with AP indicated by single arrow.
Figure 2L:
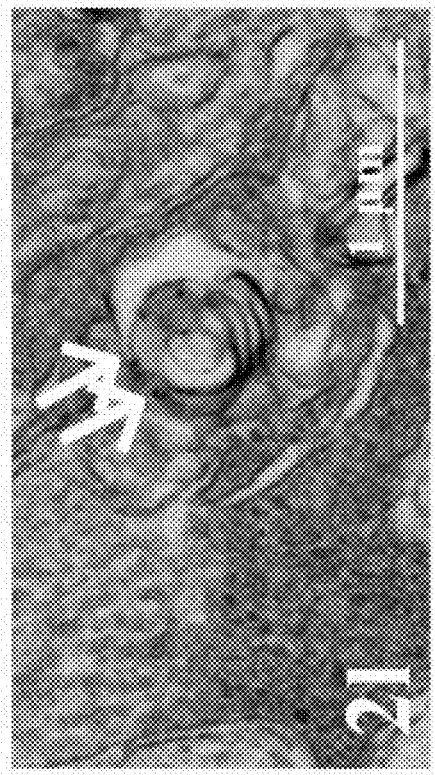
FIG. 2L discloses 1 μM AlloP with DAV indicated by double arrows.

Example 4. Autophagy Vacuoles Induced by High Pressure and Effects of Neurosteroids Because AlloP activates autophagy in primary astrocyte cultures, the activation of autophagy induced by AlloP and ent-AlloP was examined. Electron microscopy revealed that retinas incubated at 10 mmHg remained intact (FIG. 2A), while substantial swelling of axons was observed after exposure to high pressure (75 mmHg; FIG. 2B). Similar to AlloP (FIG. 2C), ent-AlloP (FIG. 2D) protected RGC axons from high pressure. Retinas were then examined for the presence of autophagosomes (APs) and degenerative autophagic vacuoles (DAVs). These structures are present even at control pressure (10 mmHg; FIG. 2E-G). Elevated pressure significantly increased numbers of APs and other autophagy components in the NFL (FIG. 2H-J). The increase in APs was robustly altered by AlloP, without effect on DAVs (FIG. 2K, 2L). Interestingly, the high pressure-mediated increase in APs was significantly decreased by ent-AlloP, while DAVs in the NFL were significantly increased (FIG. 2M). A quantitative assessment of APs and DAVs induced by pressure elevation and administration of AlloP or ent-AlloP is summarized in FIG. 2N and FIG. 2O, respectively (Table 5, 6).

TABLE 5

Figure 2N:
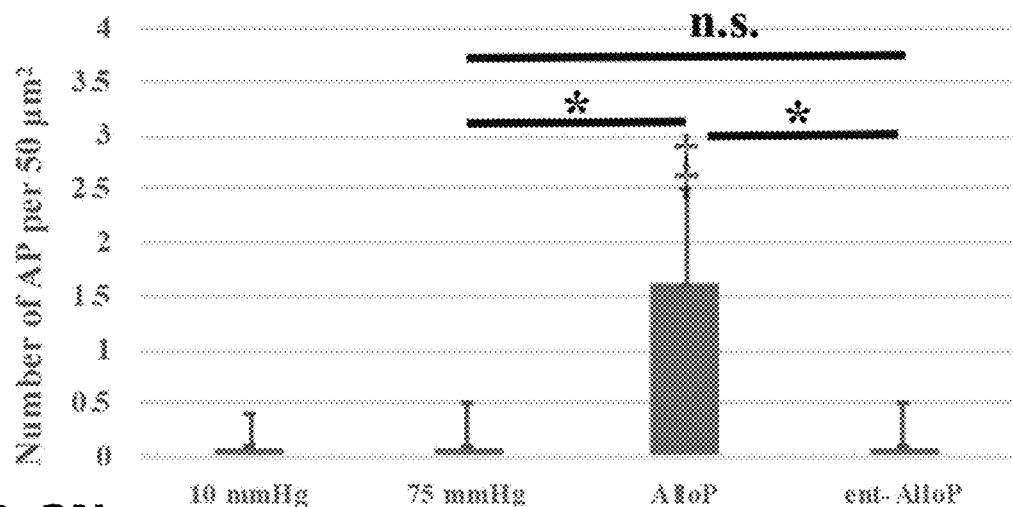
FIG. 2N discloses the number of AP per 50 μm2 of retina. (Dunnett †p<0.05 or Tukey *p<0.05).

Autophagosomes (AP)/25 µm2 in the NFL (FIG. 2N)

| | 10 mmHg | 75 mmHg | AlloP | ent-AlloP |
|---|---|---|---|---|
| 1 | 0 | 0 | 1 | 0 |
| 2 | 0 | 0 | 2 | 0 |
| 3 | 1 | 0 | 2 | 0 |
| 4 | 0 | 1 | 0 | 1 |
| 5 | 0 | 0 | 2 | 0 |
| 6 | 0 | 0 | 0 | 0 |
| 7 | 0 | 0 | 2 | 0 |
| 8 | 0 | 0 | 2 | 0 |
| 9 | 0 | 0 | 3 | 0 |
| 10 | 0 | 0 | 2 | 0 |
| Total | 1 | 1 | 16 | 1 |
| Average | 0.1 | 0.1 | 1.6 | 0.1 |
| SD | 0.3 | 0.4 | 0.9 | 0.4 |
| Dunnett | vs | p > 0.05 | <0.05* | >0.05 |
| | vs | p > 0.05 | <0.05* | >0.05 |
| Tukey | | vs | <0.05* | >0.05 |
| | | | vs | <0.05* |

TABLE 6

Figure 2O:
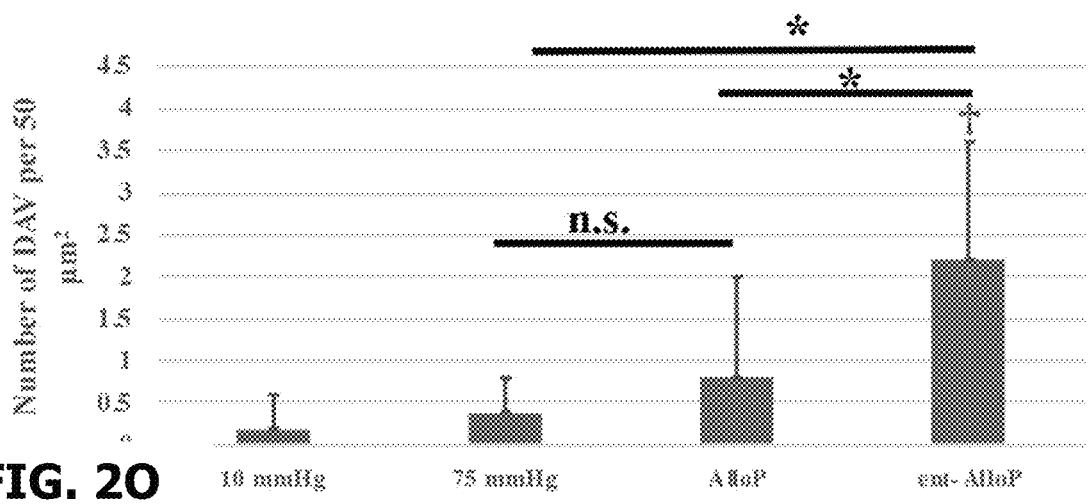
FIG. 2O discloses the number of DAV per 50 μm2 of retina (Dunnett †p<0.05 or Tukey *p<0.05).

Degenerative autophagic vacuoles (DAV)/25 µm2 in the NFL (FIG. 2O)

| | 10 mmHg | 75 mmHg | AlloP | ent-AlloP |
|---|---|---|---|---|
| 1 | 0 | 0 | 3 | 3 |
| 2 | 0 | 0 | 1 | 1 |
| 3 | 0 | 0 | 0 | 4 |
| 4 | 0 | 1 | 1 | 1 |
| 5 | 1 | 0 | 0 | 1 |
| 6 | 1 | 0 | 0 | 2 |
| 7 | 0 | 1 | 1 | 2 |
| 8 | 0 | 0 | 1 | 2 |
| 9 | 0 | 0 | 0 | 2 |
| 10 | 0 | 2 | 1 | 4 |
| Total | 2 | 4 | 8 | 22 |
| Average | 0.2 | 0.4 | 0.8 | 2.2 |
| SD | 0.4 | 0.4 | 1.2 | 1.4 |
| Dunnett | vs | >0.05 | >0.05 | <0.05* |
| | vs | >0.05 | >0.05 | <0.05* |
| Tukey | | vs | >0.05 | <0.05* |
| | | | vs | <0.05* |

Example 5. Autophagy Markers and Effects of Ent-AlloP on Autophagy Flow

Microtubule-associated protein-1 light chain 3 (LC3) is a core contributor to autophagy (FIG. 1A), playing a crucial role in elongation of phagophore membranes and serving as a marker of autophagy. LC3 antibodies displayed double bands (LC3-I and LC3-II) at approximately 14-16 kDa. Quantitative Western blot analysis demonstrated that administration of both neurosteroids significantly increased LC3-II expression compared to drug-free pressure elevation (FIG. 2P and FIG. 2Q, Table 7). Because both LC3-I and LC3-II were increased by both neurosteroids, it was necessary to examine another autophagy marker to assess changes in autophagic flow. P62 is a protein that is incorporated into completed autophagosomes and accumulates when autophagy is impaired. Although Western blot analysis demonstrated that AlloP altered expression of p62 compared to controls incubated at 75 mmHg, ent-AlloP more effectively depressed p62 compared to AlloP (FIG. 2R, 2S, Table 8).

TABLE 7

LC3-II expression (FIG. 2Q)

| | Control | OHT | AlloP | ent-AlloP |
|---|---|---|---|---|
| 1 | 1.00 | 1.50 | 4.31 | 6.14 |
| 2 | 1.00 | 2.03 | 3.47 | 5.17 |
| 3 | 1.00 | 1.23 | 3.34 | 4.48 |
| 4 | 1.00 | 2.15 | 3.34 | 5.22 |
| Average | 1.00 | 1.73 | 3.62 | 5.25 |
| SD | 0.02 | 0.45 | 0.49 | 0.70 |
| Dunnett | vs | >0.05 | <0.05* | <0.05* |
| Tukey | vs | >0.05 | <0.05* | <0.05* |
| | | vs | <0.05* | <0.05* |
| | | | vs | <0.05* |

TABLE 8 p62 expression (FIG. 2S)

| | 10 mmHg | 75 mmHg | AlloP | ent-AlloP |
|---|---|---|---|---|
| 1 | 1.00 | 3.30 | 1.96 | 0.92 |
| 2 | 1.00 | 3.16 | 2.18 | 0.40 |
| 3 | 1.00 | 4.89 | 2.05 | 1.00 |
| 4 | 1.00 | 2.08 | 0.84 | 0.28 |
| 5 | 1.00 | 3.12 | 2.81 | 1.08 |
| Average | 1.00 | 3.31 | 1.97 | 0.74 |
| SD | 0.02 | 1.18 | 0.64 | 0.38 |
| Dunnett | vs | <0.05* | >0.05 | >0.05 |
| Tukey | vs | <0.05* | >0.05 | >0.05 |
| | | vs | <0.05* | <0.05* |
| | | | vs | <0.05* |

Figures 3E, 3F, 3G, 3H:
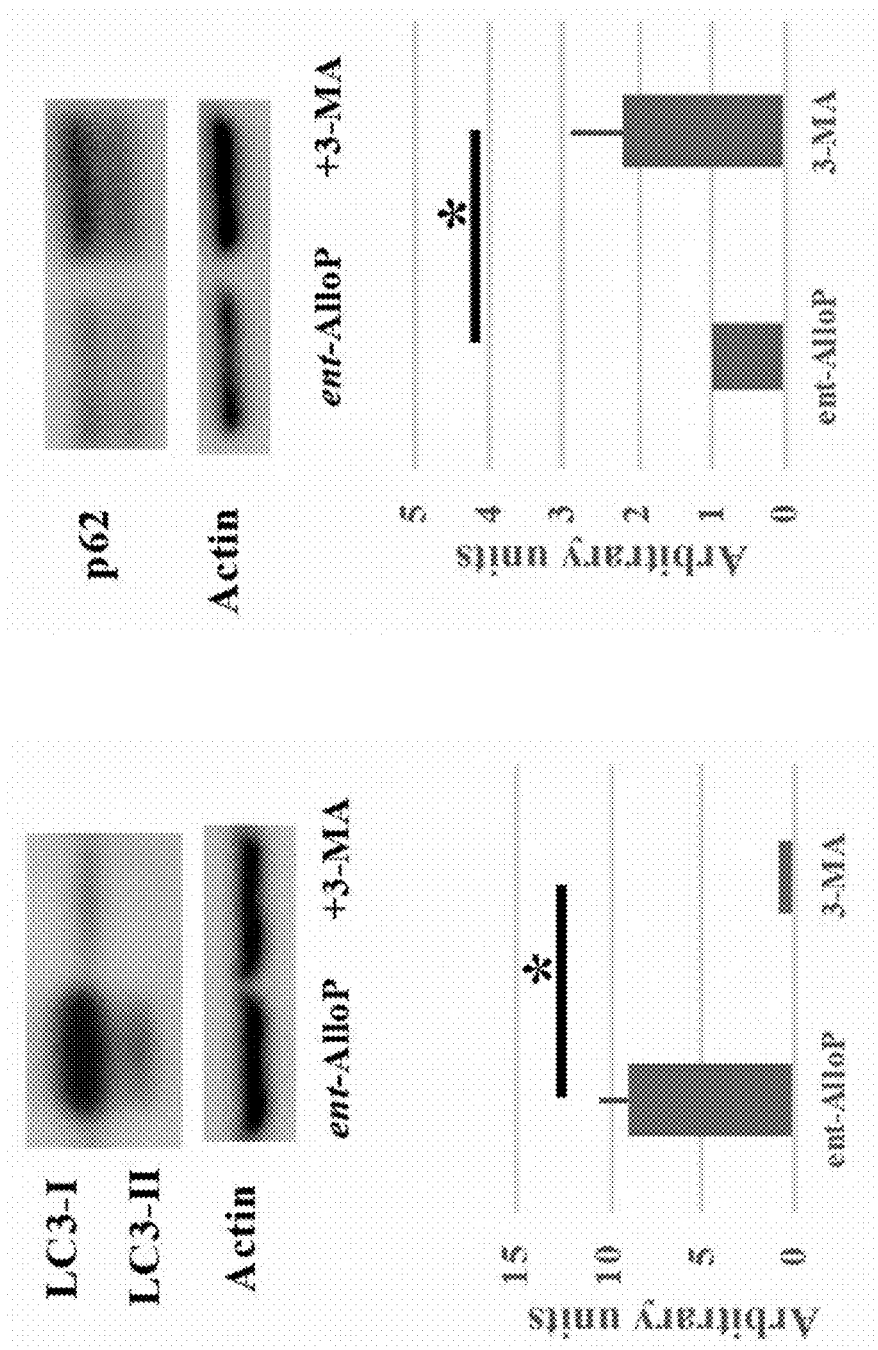
FIG. 3E discloses representative Western blot analyses of LC3 proteins in pressure-loaded retinas (75 mmHg) treated with 1 μM ent-AlloP alone or with 1 μM ent-AlloP and 10 mM 3-MA.
FIG. 3F discloses quantitative Western blot analysis of LC3-II expression in the retina incubated with ent-AlloP at 75 mmHg (Wilcoxon Rank-Sum Test *p<0.05).
FIG. 3G discloses representative Western blot analyses of p62 proteins in pressure-loaded retinas (75 mmHg) treated with 1 μM ent-AlloP alone or with 1 μM ent-AlloP and 10 mM 3-MA.
FIG. 3H discloses quantitative Western blot analysis of p62 expression.

Example 6. 3-MA Blocks Autophagy and Inhibits the Neuroprotective Effects of ent-AlloP To determine whether autophagy plays a key role in retinal protection by ent-AlloP, 3-methyladenine (3-MA), an inhibitor of autophagic flux, was examined. At 10 mM, 3-MA did not alter neuroprotection by AlloP (FIG. 3A), but dampened the effects of ent-AlloP at 75 mmHg (FIG. 3B). It was also found that 3-MA alone was neurodegenerative at both 75 mmHg (FIG. 3C) and 10 mmHg (FIG. 3D), indicating that autophagy is important for maintaining retinal integrity even under control conditions. A combination of ent-AlloP and 3-MA significantly increased the density of damaged cells in the GCL compared to controls incubated at 75 mmHg (p<0.05) and overcame the protective effects of ent-AlloP at high pressure (Table 1, Table 2). It was also examined whether 3-MA altered the effects of ent-AlloP on autophagic markers, and it was found that upregulation of LC3-II levels induced by ent-AlloP was dampened by 3-MA (FIG. 3E, 3F, Table 9). Also, the decrease of p62 levels induced by ent-AlloP at 75 mmHg was reversed by 3-MA (FIG. 3G, 3H, Table 10). Administration of 10 mM 3-MA significantly increased LC3-II expression in the retina incubated with ent-AlloP at 75 mmHg (Wilcoxon Rank-Sum Test, *p<0.05), as shown in FIG. 3(A-H). These findings indicate that ent-AlloP likely acts by enhancing autophagic flow.

TABLE 9

LC3 expression after 3-MA treatment (FIG. 3F)

| | ent-AlloP | ent-AlloP + 3-MA |
|---|---|---|
| 1 | 11.20 | 1.00 |
| 2 | 8.89 | 1.00 |
| 3 | 7.78 | 1.00 |
| 4 | 8.11 | 1.00 |
| Average | 9.00 | 1.00 |
| SD | 1.54 | 0.00 |
| Wicoxon | vs | p = 0.0139 |

TABLE 10 p62 expression after 3-MA treatment (FIG. 3H)

| | ent-AlloP | ent-AlloP + 3-MA |
|---|---|---|
| 1 | 1.00 | 3.21 |
| 2 | 1.00 | 2.11 |
| 3 | 1.00 | 1.76 |
| 4 | 1.00 | 1.66 |
| Average | 1.00 | 2.19 |
| SD | 0.00 | 0.71 |
| Wicoxon MW | vs | p = 0.0139 |

Figure 4A:
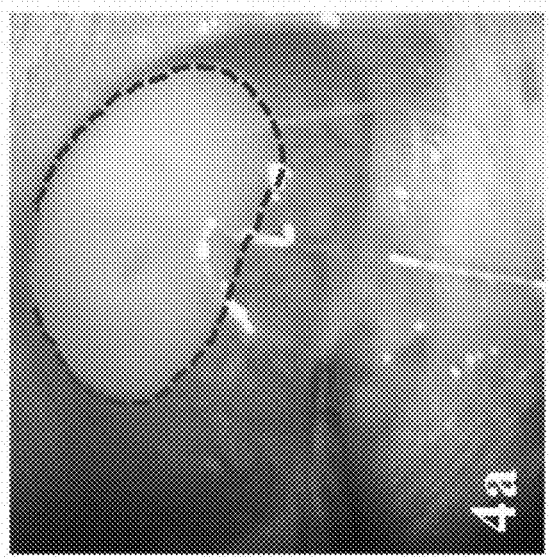
FIG. 4A discloses an injection of microbeads (surrounded by a broken line) into the anterior chamber.
Figure 4B:
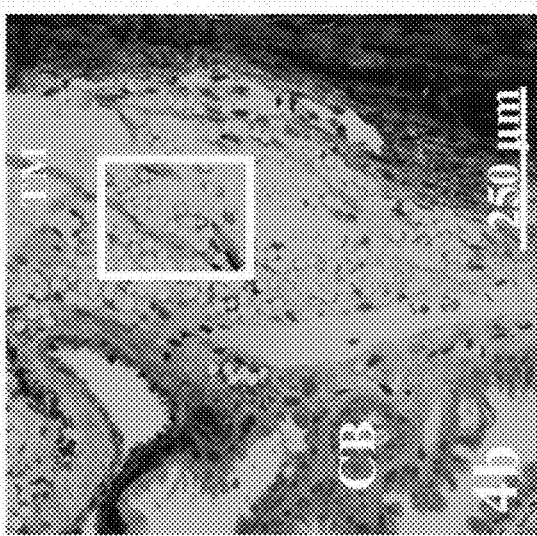
FIG. 4B discloses a light micrograph of the iridocorneal angle ("TM" indicates trabecular meshwork; "CB" indicates ciliary body).
Figure 4C:
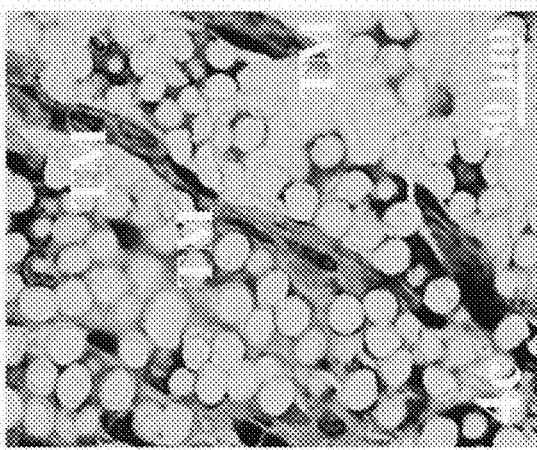
FIG. 4C discloses an enlargement of the rectangular area in FIG. 4B.
Figures 4E, 4F, 4G, 4H:
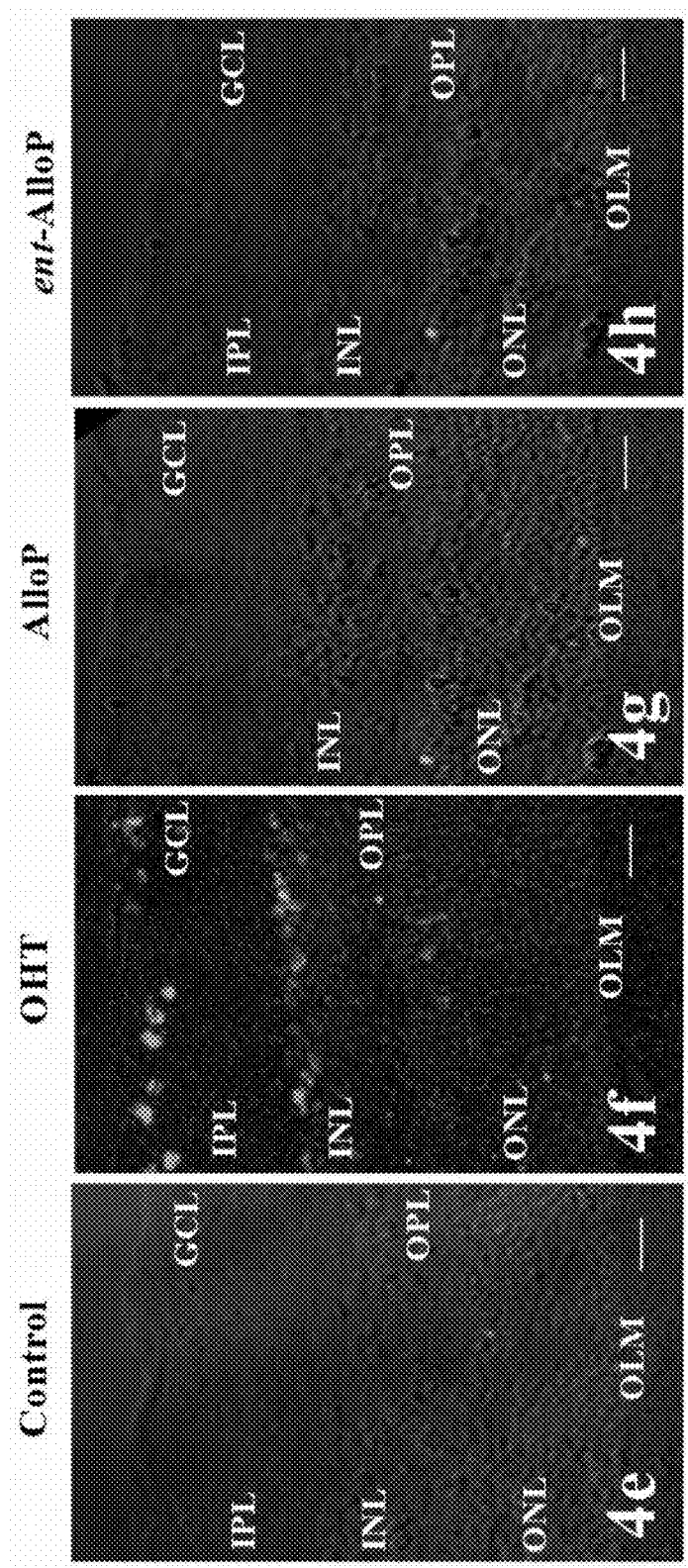
FIG. 4E discloses control eye TUNEL staining.
FIG. 4F discloses non-treated OHT eye TUNEL staining.
FIG. 4G discloses TUNEL staining for administration of 1 μM AlloP in OHT eyes, scale bars 30 μm.
FIG. 4H discloses TUNEL staining for administration of 1 μM ent-AlloP in OHT eyes, scale bars 30 μm.
Figures 4D, 4I:
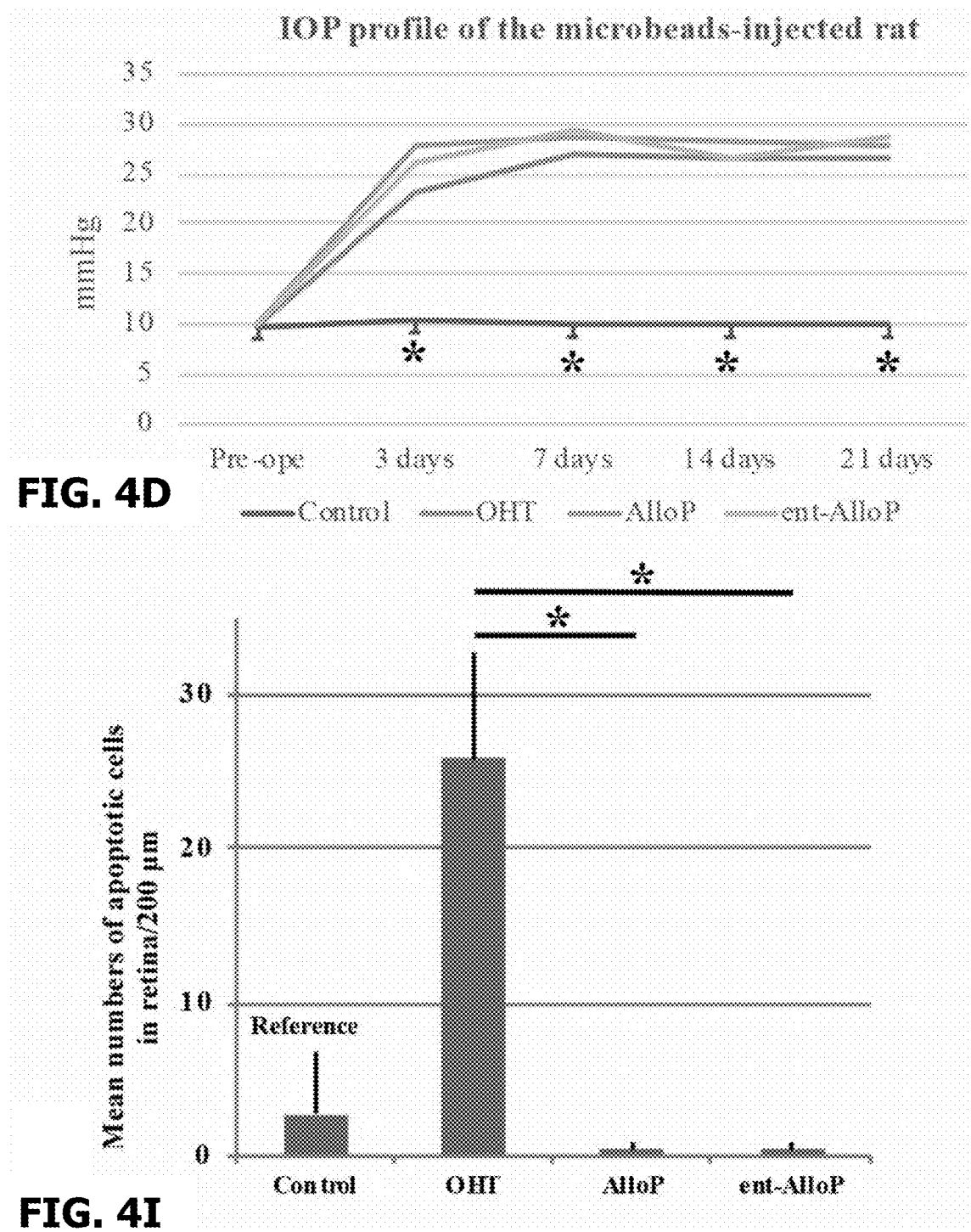
FIG. 4D discloses IOP profiles.
FIG. 4I discloses the number of TUNEL-positive RGCs per 200 μm of retinal sections (Tukey *p<0.05).

Example 7. Rat In Vivo OHT Model Induced by Intracameral Injection of Microbeads For induction of ocular hypertension (OHT) in vivo, sterile 6 μm polystyrene microbeads were injected into the anterior chamber of the left eye of each animal using a single-step, sclero-corneal tunnel approach with a 35G nanoneedle (FIG. 4A). At 3 weeks after intracameral bead injection, the beads were localized in the iridocorneal angle, especially in the inferior area (FIGS. 4B and 4C). After stabilization of elevated IOP, animals were randomly divided into 3 groups (non-treated OHT, AlloP injection, and ent-AlloP injection). AlloP and ent-AlloP were administered as a one-time intravitreal injection one week following bead injection. Non-treated OHT animals received sterile vehicle intravitreally. As a further control, vehicle was intravitreally injected 7 days after intracameral administration of 10 μl of PBS. Three weeks after bead injections, IOP was 26.7±3.7 mmHg in non-treated OHT eyes compared to 9.9±0.9 mmHg in control eyes. At each measurement time point (days 3, 7, 14, and 21), IOP in the three bead-injected groups (non-treated OHT, AlloP injection, and ent-AlloP injection) was significantly higher compared to control eyes (p<0.05, Wilcoxon Mann-Whitney test) (FIG. 4D, Tables 11A-D). The neurosteroids did not alter IOP at any measurement point.

TABLE 11A

IOP profile, AlloP (FIG. 4D)
AlloP

|   | Pre-ope | 3 days | 7 days | 14 days | 21 days |
|---|---|---|---|---|---|
| 1 | 10 | 25 | 29 | 33 | 30 |
| 2 | 11 | 31 | 33 | 36 | 25 |
| 3 | 10 | 27 | 41 | 31 | 24 |
| 4 | 11 | 25 | 36 | 31 | 33 |
| 5 | 12 | 31 | 35 | 32 | 31 |
| 6 | 9 | 25 | 30 | 25 | 24 |
| 7 | 10 | 27 | 25 | 21 | 26 |
| 8 | 10 | 28 | 21 | 19 | 27 |
| 9 | 11 | 20 | 32 | 30 | 21 |
| 10 | 10 | 25 | 21 | 27 | 33 |
| 11 | 10 | 28 | 31 | 28 | 31 |
| 12 | 10 | 22 | 25 | 25 | 30 |
| 13 | 9 | 33 | 23 | 20 | 28 |
| 14 | 9 | 30 | 20 | 36 | 25 |
| Average | 10.1 | 26.9 | 28.7 | 28.1 | 27.7 |
| SD | 0.9 | 3.6 | 6.4 | 5.6 | 3.7 |
| Dunnett | vs | $p < 0.05*$ | $p < 0.05*$ | $p < 0.05*$ | $p < 0.05*$ |

TABLE 11B

IOP profile, ent-AlloP (FIG. 4D)
ent-AlloP

|   | Pre-ope | 3 days | 7 days | 14 days | 21 days |
|---|---|---|---|---|---|
| 1 | 9 | 22 | 25 | 31 | 22 |
| 2 | 8 | 32 | 21 | 20 | 27 |
| 3 | 10 | 27 | 38 | 35 | 36 |
| 4 | 12 | 20 | 39 | 41 | 34 |
| 5 | 13 | 32 | 27 | 25 | 30 |
| 6 | 10 | 25 | 21 | 22 | 21 |
| 7 | 9 | 33 | 26 | 21 | 24 |
| 8 | 8 | 36 | 23 | 20 | 33 |
| 9 | 10 | 28 | 21 | 35 | 31 |
| 10 | 10 | 20 | 31 | 29 | 20 |
| 11 | 10 | 25 | 34 | 20 | 33 |
| 12 | 9 | 15 | 42 | 31 | 30 |
| 13 | 11 | 30 | 32 | 33 | 35 |
| 14 | 12 | 23 | 37 | 32 | 29 |
| Average | 10.1 | 26.3 | 29.8 | 28.2 | 28.9 |
| SD | 1.5 | 6.0 | 7.3 | 6.9 | 5.3 |
| Dunnett | vs | $p < 0.05*$ | $p < 0.05*$ | $p < 0.05*$ | $p < 0.05*$ |

TABLE 11C

IOP profile, OHT (FIG. 4D)
OHT (vehicle control)

|   | Pre-ope | 3 days | 7 days | 14 days | 21 days |
|---|---|---|---|---|---|
| 1 | 10 | 21 | 31 | 29 | 28 |
| 2 | 8 | 26 | 30 | 30 | 20 |
| 3 | 10 | 29 | 29 | 30 | 31 |
| 4 | 11 | 30 | 21 | 20 | 25 |
| 5 | 10 | 22 | 19 | 19 | 28 |
| 6 | 10 | 21 | 30 | 30 | 30 |
| 7 | 10 | 14 | 29 | 28 | 25 |
| 8 | 9 | 30 | 25 | 20 | 35 |
| 9 | 9 | 21 | 21 | 27 | 28 |
| 10 | 10 | 25 | 34 | 21 | 20 |
| 11 | 10 | 25 | 31 | 20 | 33 |
| 12 | 10 | 38 | 30 | 31 | 30 |
| 13 | 11 | 30 | 32 | 33 | 35 |
| 14 | 10 | 21 | 29 | 32 | 29 |
| Average | 9.9 | 23.3 | 27.0 | 26.4 | 26.7 |
| SD | 0.9 | 5.5 | 4.9 | 5.2 | 3.7 |
| Dunnett | vs | $p < 0.05*$ | $p < 0.05*$ | $p < 0.05*$ | $p < 0.05*$ |

TABLE 11D

IOP profile, intact control (FIG. 4D)
Intact control

|   | Pre-ope | 3 days | 7 days | 14 days | 21 days |
|---|---|---|---|---|---|
| 1 | 9 | 10 | 11 | 9 | 8 |
| 2 | 8 | 10 | 10 | 10 | 10 |
| 3 | 10 | 12 | 9 | 10 | 11 |
| 4 | 11 | 11 | 11 | 10 | 10 |
| 5 | 10 | 10 | 9 | 10 | 10 |
| 6 | 10 | 9 | 10 | 11 | 10 |
| 7 | 10 | 11 | 9 | 8 | 10 |
| 8 | 9 | 10 | 10 | 11 | 12 |
| 9 | 10 | 9 | 13 | 11 | 10 |
| 10 | 10 | 9 | 10 | 9 | 10 |
| 11 | 10 | 10 | 9 | 9 | 10 |
| 12 | 9 | 12 | 11 | 12 | 13 |
| 13 | 11 | 11 | 10 | 10 | 11 |
| 14 | 12 | 13 | 9 | 8 | 8 |
| Average | 9.7 | 10.4 | 9.9 | 9.9 | 9.9 |
| SD | 1.0 | 1.0 | 0.9 | 1.2 | 0.9 |
| Dunnett | vs | $p > 0.05$ | $p > 0.05$ | $p > 0.05$ | $p > 0.05$ |

Example 8. Pressure-Induced Apoptosis and Neuroprotection with ADoP and Ent-AlloP In Vivo Three weeks after intracameral administration of PBS, a few TUNEL-positive cells are observed in the INL and ONL in control eyes (FIG. 4E). In contrast, apoptosis was markedly increased in the GCL, INL, and ONL in non-treated OHT eyes (FIG. 4F). The number of TUNEL-positive cells was reduced to control levels when 1 µM AlloP (FIG. 4G) or 1 µM ent-AlloP (FIG. 4H) was administered intravitreally in the OHT eyes. The graph in FIG. 4I discloses the number of apoptotic cells in the retina in each condition (Table 12).

TABLE 12

TUNEL staining (FIG. 4I)

|   | Control | OHT | AlloP | ent-AlloP |
|---|---|---|---|---|
| 1 | 1 | 30 | 1 | 1 |
| 2 | 1 | 30 | 0 | 0 |
| 3 | 0 | 32 | 1 | 0 |
| 4 | 2 | 21 | 0 | 0 |
| 5 | 10 | 16 | 0 | 1 |
| Average | 2.8 | 25.8 | 0.4 | 0.4 |
| SD | 4.1 | 6.9 | 0.5 | 0.5 |
| Dunnett | vs | vs | $<0.05*$ | $<0.05*$ |
| Tukey | vs | vs | $<0.05*$ | $<0.05*$ |
|   |   |   | vs | $>0.05$ |

Example 9. RGC Survival by Neurosteroids During IOP Elevation

In whole mounted retinas, glaucomatous damage was visible as reduced numbers of cells that were positive for NeuN three weeks after microbead injection in non-treated OHT eyes compared with control eyes (FIG. 4J, 4K). Administration of AlloP (FIG. 4L) or ent-AlloP (FIG. 4M) prevented the loss of NeuN-positive RGCs in OHT eyes. RGC density at each pressure is summarized in FIG. 4N (Table 13). In sections of optic nerves stained with 2% toluidine blue, axonal loss was detected 3 weeks after microbead injection in non-treated OHT eyes compared with control eyes (FIG. 4O, 4p). However, administration of AlloP (FIG. 4Q) or ent-AlloP (FIG. 4R) induced significant protective effects in OHT eyes. The density of axons in each experiment is summarized in FIG. 4S (Table 14).

TABLE 13

RGC Survival (FIG. 4N)

|   | Control | OHT | AlloP | ent-AlloP |
|---|---|---|---|---|
| 1 | 2420 | 1020 | 2200 | 2060 |
| 2 | 2840 | 1240 | 2240 | 2260 |
| 3 | 1920 | 780 | 1940 | 2500 |
| 4 | 2060 | 840 | 1860 | 2200 |
| 5 | 2020 | 900 | 1800 | 2460 |
| Average | 2252.0 | 956.0 | 2008.0 | 2296.0 |
| SD | 379.1 | 181.9 | 200.3 | 183.5 |
| Dunnett | | vs | <0.05* | <0.05* |
| Tukey | | vs | <0.05* | <0.05* |
| | | | vs | >0.05 |

TABLE 14

Figure 4S:
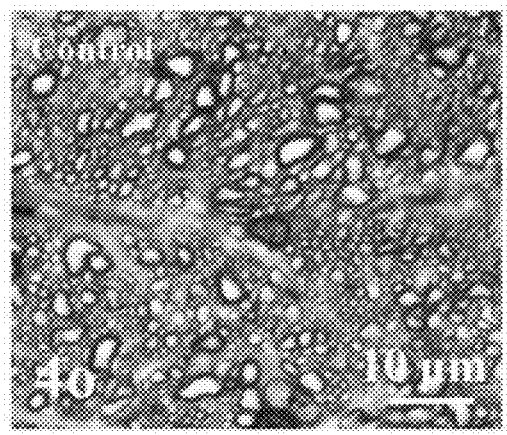
FIG. 4S discloses axonal number in whole mount retinas under each condition (Tukey *p<0.05).
Figure 4S:
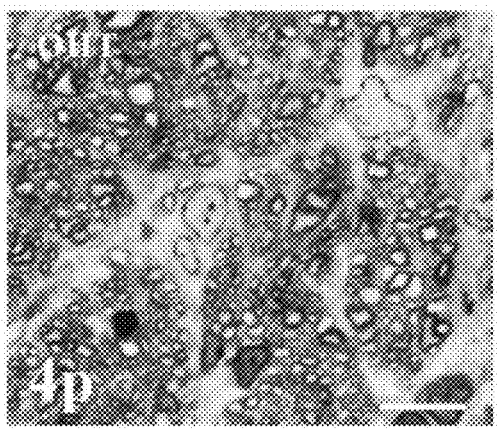
Figure 4S:
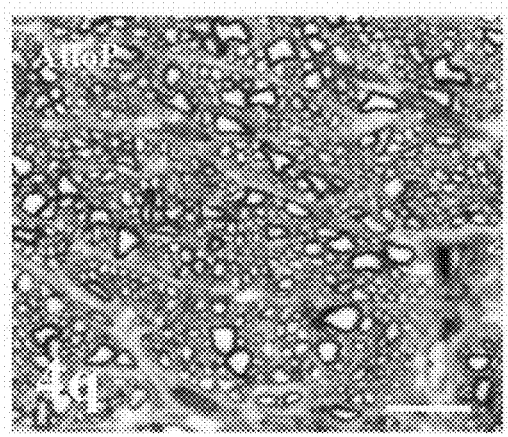
Figure 4S:
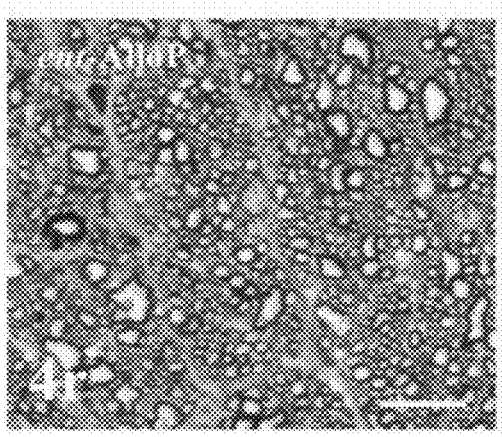
Figure 4S:
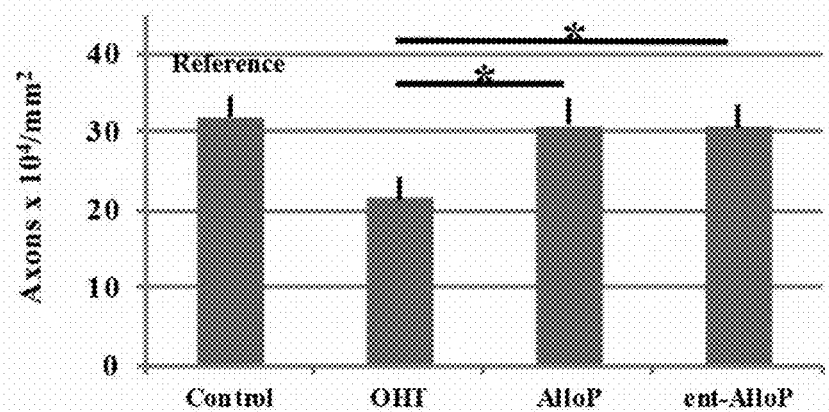

Density of axons in ONs (Axons × 10000/square mm) (FIG. 4S)

|   | Control | OHT | AlloP | ent-AlloP |
|---|---|---|---|---|
| 1 | 29 | 16 | 27 | 33 |
| 2 | 33 | 18 | 32 | 32 |
| 3 | 32 | 15 | 29 | 29 |
| 4 | 35 | 21 | 33 | 27 |
| 5 | 28 | 19 | 33 | 31 |
| Average | 31.4 | 17.8 | 30.8 | 30.4 |
| SD | 2.9 | 2.4 | 2.7 | 2.4 |
| Dunnett | | vs | <0.05* | <0.05* |
| Tukey | | vs | <0.05* | <0.05* |
| | | | vs | >0.05 |

Example 10. Autophagy Vacuoles by IOP Elevation and Effects of Neurosteroids

Figure 5D:
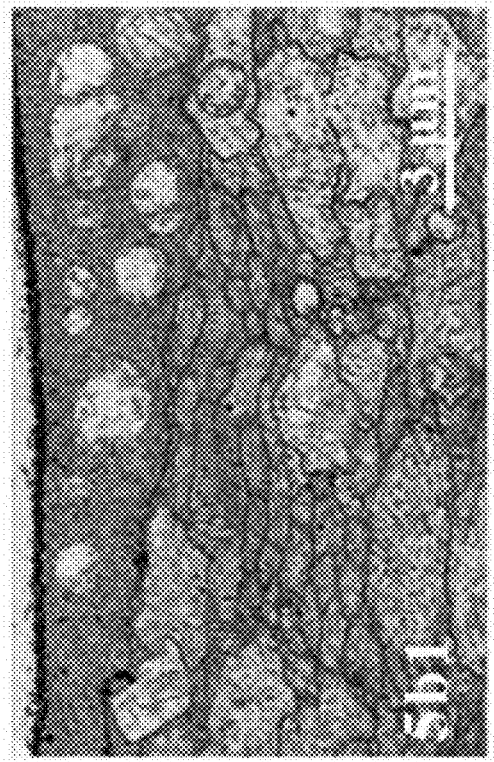
FIG. 5D discloses an electron micrograph of the NFL of a non-treated OHT eye at low magnification.
Figures 5E, 5F:
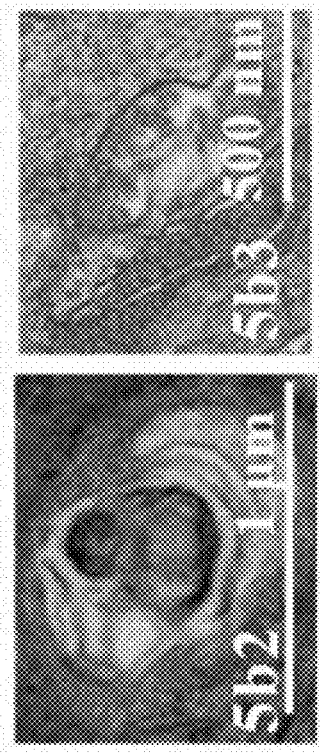
FIG. 5E discloses an electron micrograph of DAV of the non-treated OHT eye of FIG. 5D.
FIG. 5F discloses an electron micrograph of AP of the non-treated OHT eye of FIG. 5D.
Figure 5A:
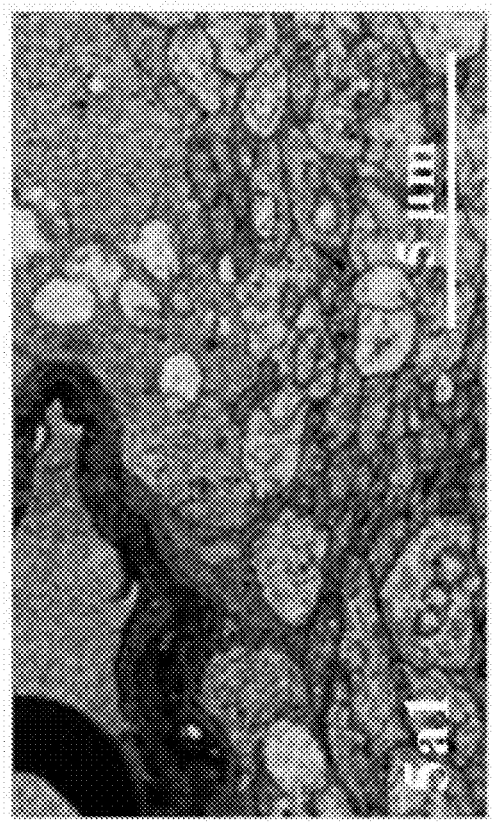
FIG. 5A discloses an electron micrograph of the NFL of a control eye at low magnification.
Figures 5B, 5C:
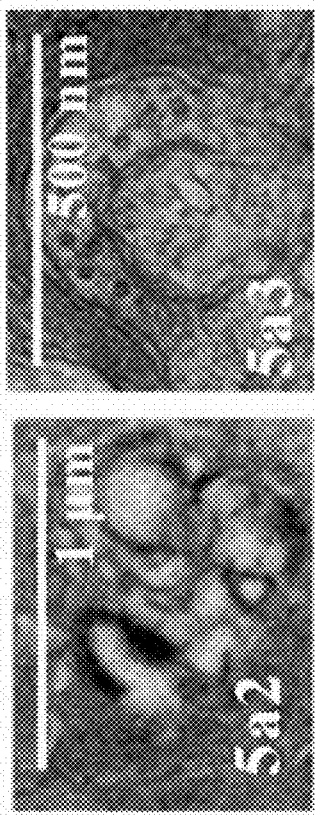
FIG. 5B discloses an electron micrograph of DAV of the control eye of FIG. 5A.
FIG. 5C discloses an electron micrograph of the isolation membrane of the control eye of FIG. 5A.

Electron microscopy revealed the presence of APs and DAVs in the NFL of control eyes (FIG. 5A,5B,5C) and OHT eyes (FIG. 5D,5E,5F). AlloP significantly increased the number of APs in the NFL in OHT eyes (FIG. 5G,5H,5I), while ent-AlloP significantly decreased the number of APs compared to AlloP-treated OHT eyes (FIG. 5J,5K,5L). DAVs in the NFL were significantly increased by 1 μM ent-AlloP compared to non-treated OHT eyes. A quantitative assessment of APs and DAVs induced by OHT and administration of AlloP or ent-AlloP is summarized in FIG. 5M and FIG. 5N, respectively (Table 15, 16).

TABLE 15

Figure 5M:
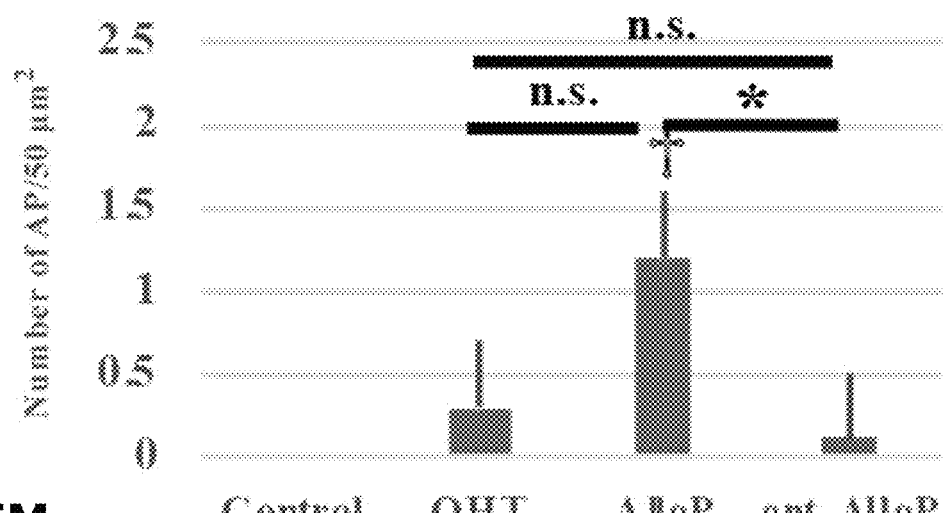
FIG. 5M discloses the number of APs (n=4 per experiment, Dunnet †p<0.05, Tukey *p<0.05).

Autophagosomes (AP)/25 μm2 in the NFL (FIG. 5M)

|   | Control | OHT | AlloP | ent-AlloP |
|---|---|---|---|---|
| 1 | 0 | 1 | 1 | 0 |
| 2 | 0 | 0 | 1 | 0 |

TABLE 15-continued

Autophagosomes (AP)/25 μm2 in the NFL (FIG. 5M)

|   | Control | OHT | AlloP | ent-AlloP |
|---|---|---|---|---|
| 3 | 0 | 0 | 1 | 0 |
| 4 | 0 | 0 | 1 | 0 |
| 5 | 0 | 0 | 2 | 1 |
| 6 | 0 | 1 | 2 | 0 |
| 7 | 0 | 0 | 1 | 0 |
| 8 | 0 | 0 | 1 | 0 |
| 9 | 0 | 0 | 1 | 0 |
| 10 | 0 | 1 | 1 | 0 |
| Total | 0 | 3 | 12 | 1 |
| Average | 0.0 | 0.3 | 1.2 | 0.1 |
| SD | 0.0 | 0.4 | 0.4 | 0.4 |
| Dunnett | vs | p > 0.05 | *p < 0.05 | p > 0.05 |
| Tukey | vs | p > 0.05 | *p < 0.05 | p > 0.05 |
| | | vs | *p < 0.05 | p > 0.05 |
| | | | vs | *p < 0.05 |

TABLE 16

Figure 5N:
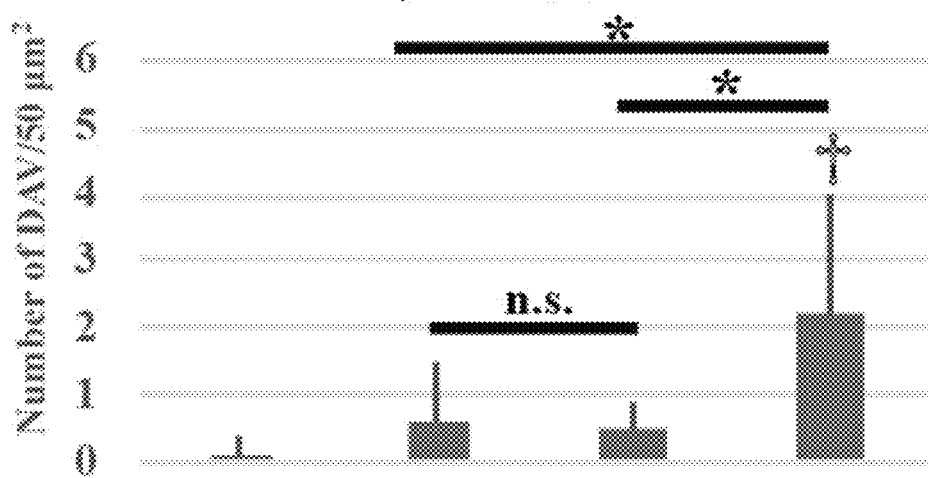
FIG. 5N discloses the number of DAVs (n=4 per experiment, Dunnet †p<0.05, Tukey *p<0.05).

Degenerative autophagic vacuoles (DAV)/25 μm2 in the NFL (FIG. 5N)

|   | Control | OHT | AlloP | ent-AlloP |
|---|---|---|---|---|
| 1 | 0 | 1 | 1 | 4 |
| 2 | 0 | 2 | 0 | 4 |
| 3 | 0 | 0 | 0 | 3 |
| 4 | 0 | 0 | 0 | 0 |
| 5 | 1 | 0 | 0 | 1 |
| 6 | 0 | 1 | 2 | 2 |
| 7 | 0 | 0 | 0 | 2 |
| 8 | 0 | 1 | 2 | 2 |
| 9 | 0 | 1 | 0 | 2 |
| 10 | 0 | 0 | 0 | 2 |
| Total | 1 | 6 | 5 | 22 |
| Average | 0.1 | 0.6 | 0.5 | 2.2 |
| SD | 0.3 | 0.9 | 0.4 | 1.8 |
| Dunnett | vs | p > 0.05 | p > 0.05 | *p < 0.05 |
| Tukey | vs | p > 0.05 | p > 0.05 | *p < 0.05 |
| | | vs | p > 0.05 | *p < 0.05 |
| | | | vs | *p < 0.05 |

Figures 5P, 5Q, 5R:
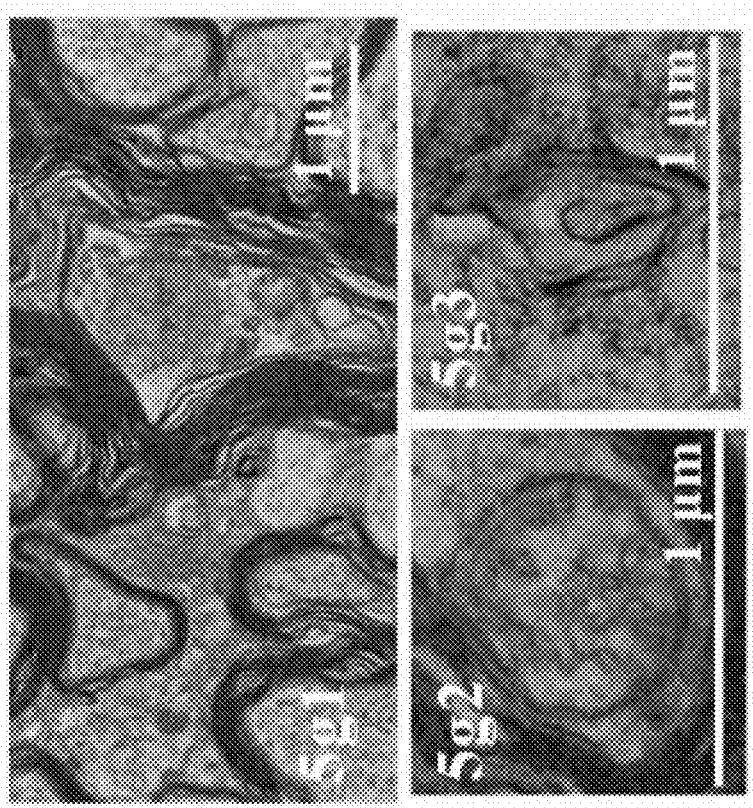
FIG. 5P discloses an electron micrograph of an OHT eye at low magnification.
FIG. 5Q discloses an electron micrograph of AP of the OHT eye of FIG. 5P.
FIG. 5R discloses an electron micrograph of DAV of the OHT eye of FIG. 5P.
Figure 5O:
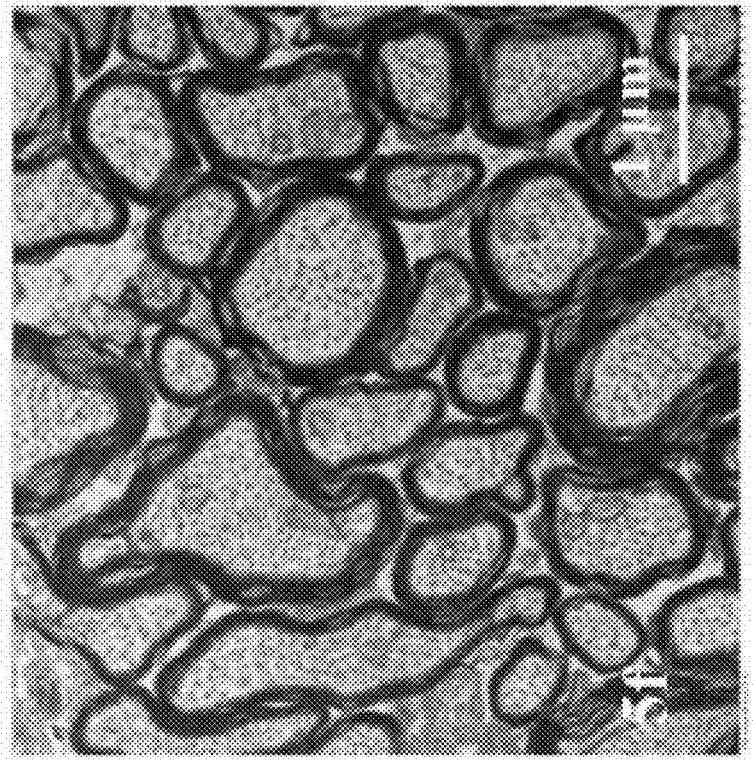
FIG. 5O discloses an electron micrograph of optic nerves of a control eye.

APs and DAVs were also observed in the optic nerves (ON) of control eyes (FIG. 5O). Compared to non-treated OHT eyes (FIG. 5P,5Q,5R), the number of APs significantly increased in the ON of OHT eyes (FIG. 5S,5T,5U), while ent-Allop significantly decreased APs (FIG. 5V,5W,5X). DAVs in the ON were significantly increased by administration of 1 μM ent-AlloP compared to non-treated OHT eyes. A quantitative assessment of Aps and DAVs in the ON induced by OHT and administration of AlloP or ent-AlloP is summarized in FIG. 5Y and FIG. 5Z, respectively (Table 17, 18).

TABLE 17

Figure 5Y:
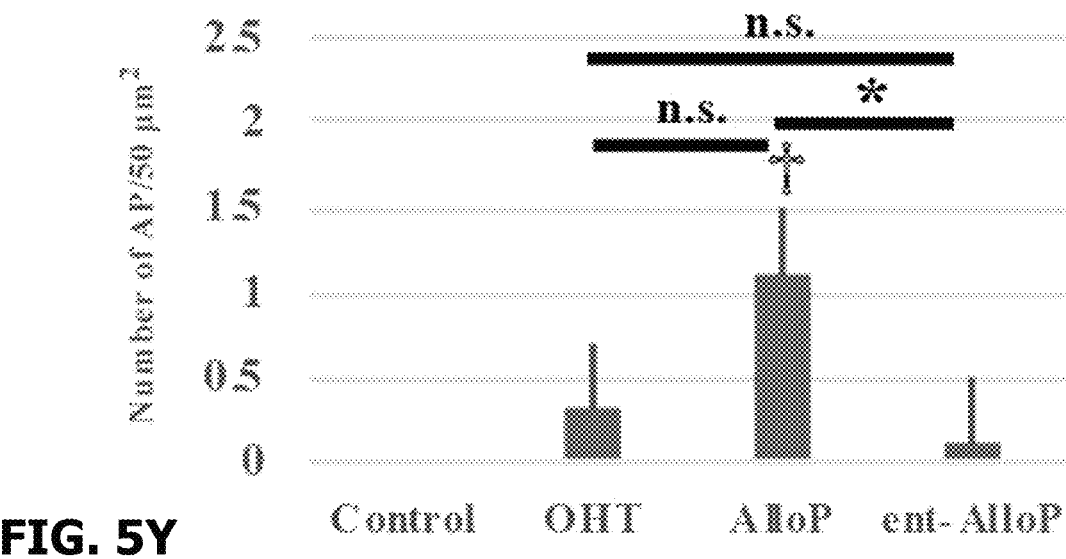
FIG. 5Y discloses the number of APs and FIG. 5Z discloses the number of DAVs *p<0.05.

Autophagosomes (AP)/100 μm2 in the ON (FIG. 5Y)

|   | Control | OHT | AlloP | ent-AlloP |
|---|---|---|---|---|
| 1 | 0 | 0 | 1 | 0 |
| 2 | 0 | 1 | 1 | 1 |
| 3 | 0 | 0 | 1 | 0 |
| 4 | 0 | 0 | 1 | 0 |
| 5 | 0 | 0 | 2 | 0 |
| 6 | 0 | 1 | 1 | 0 |

TABLE 17-continued

Autophagosomes (AP)/100 μm2 in the ON (FIG. 5Y)

|  | Control | OHT | AlloP | ent-AlloP |
|---|---|---|---|---|
| 7 | 0 | 0 | 1 | 0 |
| 8 | 0 | 0 | 1 | 0 |
| 9 | 0 | 0 | 1 | 0 |
| 10 | 0 | 1 | 1 | 0 |
| Average | 0.0 | 0.3 | 1.1 | 0.1 |
| SD | 0.0 | 0.4 | 0.4 | 0.4 |
| Dunnett | vs | p > 0.05 | *p < 0.05 | p > 0.05 |
| Tukey | vs | p > 0.05 | *p < 0.05 | p > 0.05 |
|  |  | vs | *p < 0.05 | p > 0.05 |
|  |  |  | vs | *p < 0.05 |

TABLE 18

Figure 5Z:
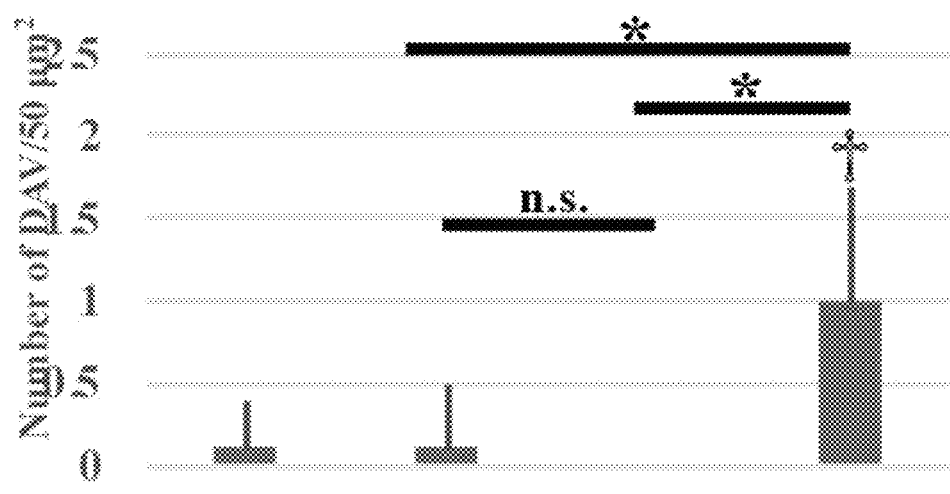
FIGS. 5(A-Z) are exemplary embodiments of electron micrographs in in vivo OHT eyes in accordance with the present disclosure.
FIG. 5G discloses an electron micrograph of the NFL of an OHT eye treated with AlloP at low magnification.
FIG. 5H discloses an electron micrograph of DAV of the of OHT eye treated with AlloP of FIG. 5G.
FIG. 5I discloses an electron micrograph of AP (indicated by arrowhead) and DAV (indicated by double arrows) of the OHT eye treated with AlloP of FIG. 5G.
FIG. 5J discloses an electron micrograph of the NFL of an OHT eye treated with ent-AlloP at low magnification.
FIG. 5K discloses an electron micrograph of DAV of the OHT eye treated with ent-AlloP of FIG. 5J.
FIG. 5L discloses an electron micrograph of DAV of the OHT eye treated with ent-AlloP of FIG. 5J.
FIG. 5S discloses an electron micrograph of an OHT eye treated with AlloP at low magnification.
FIG. 5T discloses an electron micrograph of AP of the OHT eye treated with AlloP of FIG. 5S.
FIG. 5U discloses an electron micrograph of AP of the OHT eye treated with AlloP of FIG. 5S.
FIG. 5V discloses an electron micrograph of an OHT eye treated with ent-AlloP at low magnification.
FIG. 5W discloses an electron micrograph of DAV of the OHT eye treated with ent-AlloP of FIG. 5V.
FIG. 5X discloses an electron micrograph of DAV of the OHT eye treated with ent-AlloP of FIG. 5V.

Degenerative autophagic vacuoles (DAV)/100 μm2 in the ON (FIG. 5Z)

|  | Control | OHT | AlloP | ent-AlloP |
|---|---|---|---|---|
| 1 | 0 | 0 | 0 | 1 |
| 2 | 0 | 0 | 0 | 1 |
| 3 | 0 | 1 | 0 | 1 |
| 4 | 0 | 0 | 0 | 2 |
| 5 | 1 | 0 | 0 | 0 |
| 6 | 0 | 0 | 0 | 1 |
| 7 | 0 | 0 | 0 | 1 |
| 8 | 0 | 0 | 0 | 1 |
| 9 | 0 | 0 | 0 | 1 |
| 10 | 0 | 0 | 0 | 1 |
| Average | 0.1 | 0.1 | 0.0 | 1.0 |
| SD | 0.3 | 0.4 | 0.0 | 0.7 |
| Dunnett | vs | p > 0.05 | p > 0.05 | *p < 0.05 |
| Tukey | vs | p > 0.05 | p > 0.05 | *p < 0.05 |
|  |  | vs | p > 0.05 | *p < 0.05 |
|  |  |  | vs | *p < 0.05 |

Figure 6A:
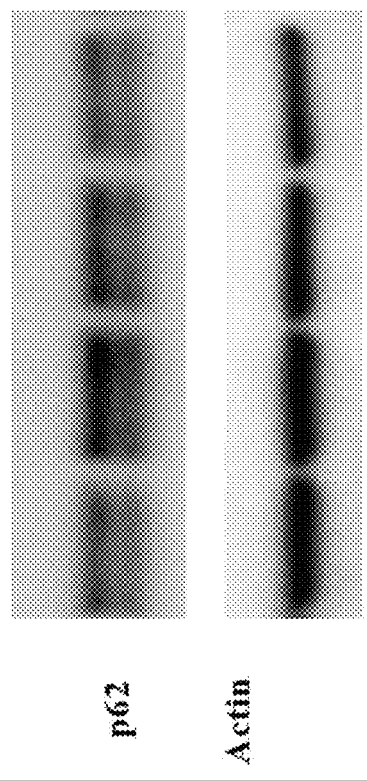
FIG. 6A discloses Western blot analysis of LC3.
Figure 6C:
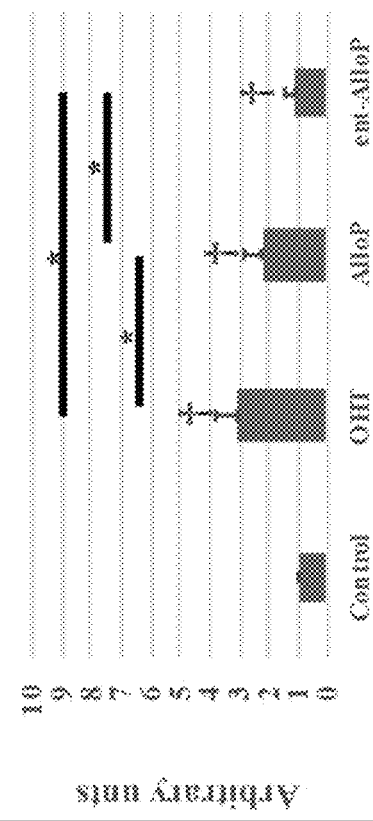
FIG. 6C discloses Western blot analysis of p62.
Figure 6B:
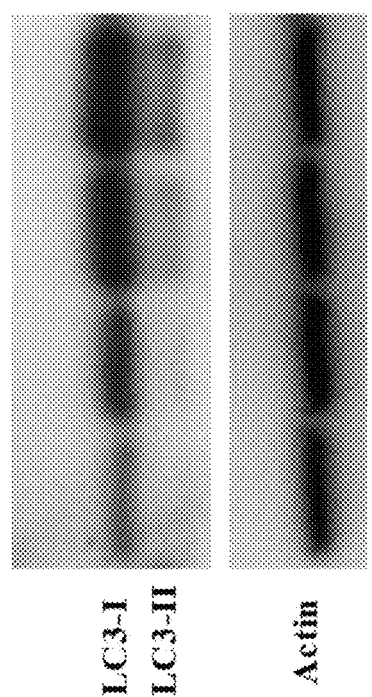
FIG. 6B discloses quantitative analysis of LC3-II expression (n=4 per experiment, Dunnet †p<0.05, Tukey *p<0.05). *p<0.05.
Figure 6D:
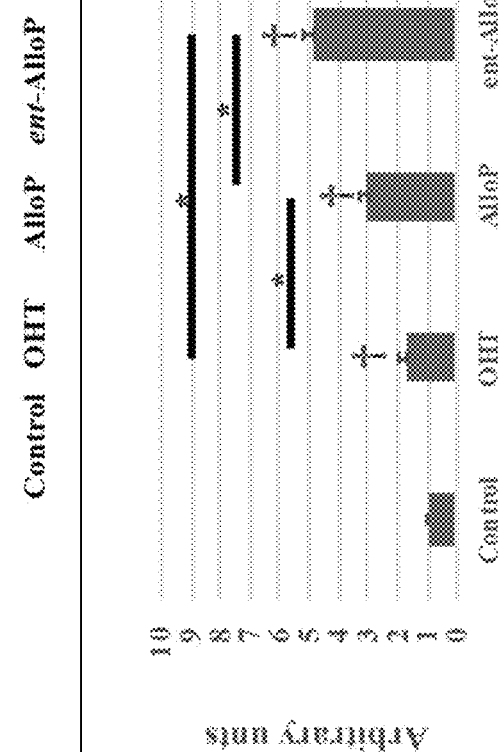
FIG. 6D discloses quantitative analysis of LC3-II expression (n=4 per experiment, Dunnet †p<0.05, Tukey *p<0.05).

Example 11. Autophagy Markers after IOP Elevation and Effects of Neurosteroids Quantitative Western blot analysis demonstrated that the level of LC3-II significantly increased in OHT eyes compared to control eyes three weeks after microbead injection (FIG. 6A, 6B, Table 19). In addition, 1 μM ent-AlloP significantly increased the level of LC3-II compared to OHT eyes treated with AlloP or OHT without neurosteroid administration 3 weeks after microbead injection (FIG. 6A, FIG. 6B, Table 19). Western blotting also demonstrated that p62 was significantly increased in eyes with OHT compared with control eyes 3 weeks after microbead injection (FIG. 6C, 6D, Table 20). Administration of 1 μM AlloP or 1 μM ent-AlloP significantly depressed the level of p62 compared to OHT eyes without neurosteroid administration (FIG. 6D, Table 20).

TABLE 19

LC3-II expression (FIG. 6B)

|  | 10 mmHg | 75 mmHg | AlloP | ent-AlloP |
|---|---|---|---|---|
| 1 | 1.00 | 1.36 | 2.73 | 4.96 |
| 2 | 1.00 | 2.00 | 3.32 | 4.97 |
| 3 | 1.00 | 1.53 | 2.82 | 4.27 |
| 4 | 1.00 | 1.77 | 3.11 | 5.04 |
| Average | 1.00 | 1.67 | 3.00 | 4.81 |

TABLE 19-continued

LC3-II expression (FIG. 6B)

|  | 10 mmHg | 75 mmHg | AlloP | ent-AlloP |
|---|---|---|---|---|
| SD | 0.02 | 0.30 | 0.29 | 0.38 |
| Dunnett | vs | <0.05* | <0.05* | <0.05* |
| Tukey | vs | <0.05* | <0.05* | <0.05* |
|  |  | vs | <0.05* | <0.05* |
|  |  |  | vs | <0.05* |

TABLE 20 p62 expression (FIG. 6D)

|  | Control | OHT | AlloP | ent-AlloP |
|---|---|---|---|---|
| 1 | 1.00 | 2.86 | 1.73 | 0.92 |
| 2 | 1.00 | 2.40 | 1.82 | 0.91 |
| 3 | 1.00 | 4.07 | 2.90 | 1.00 |
| 4 | 1.00 | 2.96 | 2.53 | 1.61 |
| Average | 1.00 | 3.07 | 2.25 | 1.11 |
| SD | 0.02 | 0.73 | 0.58 | 0.35 |
| Dunnett | vs | <0.05* | <0.05* | >0.05 |
| Tukey | vs | <0.05* | <0.05* | >0.05 |
|  |  | vs | >0.05 | <0.05* |
|  |  |  | vs | <0.05* |

Discussion

These results demonstrate the therapeutic effect of AlloP enantiomers and the involvement of autophagy as a protective mechanism in glaucoma. Although apoptosis is believed to be a mechanism that kills RCGs in glaucoma, autophagy may serve either a neurotoxic or neuroprotective role. Indeed, autophagy often coexists with apoptosis in glaucoma models. Eight weeks after IOP elevation, an increase in LC3-II/I ratio was noted in rat RGCs. Because LC3-II is associated with autophagosome formation, the increased ratio indicates induction of autophagy. Autophagic vacuoles were also detected in axons of rat optic nerves 3 weeks after IOP elevation.

Similarly, autophagy in RGCs has been observed in a rhesus monkey OHT glaucoma model. In an ex vivo glaucoma model, apoptotic RGCs were observed along with modest increases in DAVs and an increase in LC3-II consistent with autophagy induction. (FIG. 5M-N and FIG. 6B). These changes were manifest by 24 hours after pressure elevation, consistent with findings that autophagy induction in RGCs occurs soon after acute axonal injury. It remains uncertain whether autophagy in RGCs is neuroprotective or neurodegenerative. While apoptosis is described as type I programmed cell death (PCD), autophagy is considered to be a type II PCD, possibly contributing to RGC death. Autophagy activation in RGCs results in apoptosis, suggesting that autophagy is neurodegenerative. Similarly, in a model of dementia, inhibition of early autophagy with 3-MA is neuroprotective, suggesting that autophagy contributes to neuronal damage. However, the primary role of autophagy is to promote cell survival by recycling cellular debris, resulting in neuroprotection, as observed in a mouse model of optic nerve transection.

Similarly, in a rat chronic hypertensive model, rapamycin, an activator of autophagy, aids RGC survival. Rapamycin also protects RGCs from damage induced by ROS. 3-MA was found to be neurodegenerative even in controls, indicating that inhibiting autophagy can have deleterious effects in the retina, and 3-MA induced degeneration of RGC was observed at both high (FIG. 3C) and low pressure (FIG. 3D).

As disclosed herein, the enantiomers of AlloP were similarly neuroprotective in both ex vivo and in vivo OHT models. AlloP and ent-AlloP are mirror image molecules that have markedly different effects on $GABA_A$ receptors. Consistent with this, it was found that picrotoxin, an inhibitor of $GABA_A$ receptors, discriminates between the neuroprotection of these enantiomers. While picrotoxin prevents the neuroprotective effects of AlloP at high pressure (FIG. 1H), it did not affect neuroprotection by ent-AlloP (FIG. 1I), indicating that neuroprotection by ent-AlloP is distinct from $GABA_A$ receptors. This observation led to consideration of alternative mechanisms for ent-AlloP.

In electron microscopic (TEM)-based analyses, ent-AlloP decreased APs but robustly increased DAVs in the NFL, indicating activation of autophagy flow. Although AlloP had partial effects on the increase in APs, AlloP failed to increase DAVs. These observations indicate that ent-AlloP exerts axonal protection via autophagy activation more effectively than AlloP, and also indicate that activation of autophagy by high pressure alone, without AlloP or ent-AlloP, is insufficient to protect RGCs from high pressure-driven damage.

These observations were confirmed with LC3 and p62 analyses. Because cytosolic LC3-I is conjugated to phosphatidyl ethanolamine to form LC3-II, LC3-II can be increased even if autophagy flow is not fully activated, consistent with the increase in LC3-II that was observed with AlloP. However, the effects of ent-AlloP are more prominent than those of AlloP (FIG. 2R-S). To determine the involvement of autophagy in neuroprotection by ent-AlloP, the effects of 3-MA on LC3 proteins were examined. 3-MA blocks autophagy by inhibiting class III phosphatidylinositol 3-kinase (PtdIns3K), an enzyme required for the membrane dynamics involved in autophagic vesicle trafficking, thus preventing formation of autophagosomes. It was found that 3-MA attenuated LC3-II upregulation (FIG. 3D) induced by ent-AlloP. p62 levels inversely correlate with autophagy activity, and when autophagy is inhibited p62 accumulates. Under pathological conditions, there is a constitutively high level of p62, leading to accumulation of damaged mitochondria and subsequent ROS production. Thus, the reduction of p62 expression by ent-AlloP (FIG. 2R) and the enhancement by 3-MA (FIG. 3E) indicate again the effective activation of autophagy flow by ent-AlloP. In the ex vivo glaucoma model described herein, it is concluded that autophagy induced by high pressure alone is not sufficient to prevent apoptosis. However, ent-AlloP successfully promotes autophagy and prevents apoptosis in high pressure.

Using a rat in vivo OHT glaucoma model, the neuroprotective effects of ent-AlloP via autophagy were further demonstrated. As in the ex vivo model, promotion of RGC survival and protection against apoptosis in OHT are similar between AlloP and ent-AlloP. However, ent-AlloP decreased AP numbers but robustly increased DAV numbers in the NFL and ON, while AlloP increased AP numbers, but did not alter DAVs. These findings indicate again that ent-AlloP activates autophagy flow more effectively than AlloP, and a significant increase in LC3-II with high pressure is shown. Additionally, ent-AlloP increased levels of LC3-II and decreased p62 in the OHT retinas.

From these observations, it is concluded that autophagy occurring in OHT is neuroprotective rather than neurodegenerative, but, in the absence of augmentation by ent-AlloP, pressure-driven autophagy is insufficient to protect the retina. It is also concluded that both AlloP and ent-AlloP serve as potential therapeutic agents for treatment of glaucoma but that these enantiomers act by distinct mechanisms, providing unique advantages to one or the other enantiomer in different clinical situations. The compounds or neurosteroids of the present disclosure are useful for at least inducing autophagy, attenuating pressure-induced retinal injury, and other benefits described herein in a subject, e.g., a human subject, and are preferably administered in the form of an effective amount of a compound (or combination of compounds) of the instant disclosure and optionally or additional components. These results also have implications for the development of neurosteroids as treatments for other neurodegenerative disorders.

Materials and Methods—

Protocols for animal use were approved by the Akita University Animal Studies Committee in accordance with the guidelines of the Policies on the Use of Animals and Humans in Neuroscience Research.

Rat Ex Vivo Eyecup Preparation—

Rat ex vivo eyecups were prepared from 28-32 day old male Sprague-Dawley rats (Charles River Laboratories International Inc., Wilmington, Mass.). The anterior half of the enucleated eyes was carefully removed to make eyecup preparations. Eyecups were placed at the bottom of a 100 ml glass beaker filled with aCSF (artificial cerebrospinal fluid) containing (in mM): 124 NaCl, 5 KCl, 2 $MgSO_4$, 2 $CaCl_2$, 1.25 $NaH_2PO_4$, 22 $NaHCO_3$, and 10 glucose, and incubated at 30° C. for 24 hours using a closed pressure-loading system (FIG. 1C). pH was maintained at 7.35 to 7.40. In the closed-pressure system, a glass beaker with the eyecup was placed at the bottom of an acrylic pressure chamber (2,000 ml volume). A 95% $O_2$-5% $CO_2$ gas mixture was delivered through disposable plastic tubing with an infusion valve and a control dial on the lid of the pressure chamber and an air filter (Cat # SLGP033RS, Merck Millipore, Billerica, Mass.). The plastic tubing delivering the gas terminated 1 cm above the bottom of the beaker.

Acutely prepared eyecups were incubated in gassed aCSF for at least 1 h at 30° C. before pressure loading. In some experiments, AlloP (1 µM), ent-AlloP (1 µM), and 3-MA (10 mM) were dissolved in aCSF at the time of experiment and administered by bath perfusion. Eyecup preparations were treated with these drugs for 1 h at 30° C. before pressure loading. For pressure loading, the 95% $O_2$-5% $CO_2$ gas mixture was infused until the pressure reading given by a manometer reached the appropriate level. The pressure was then locked by adjusting the control dial of the effusion valve, and monitored continuously for 24 h at 30° C. After maintaining the chamber at the set pressure (10 mmHg and 75 mmHg) for the indicated time, the pressure inside the chamber was carefully decreased by opening the effusion valve.

Rat In Vivo OHT Model—

8-week old male Sprague-Dawley rats were deeply anesthetized with an intraperitoneal injection of a mixture of medetomidine hydrochloride (Cat #133-17474, CAS. No 86347-15-1, Wako Pure Chemical Industries Ltd., Osaka, Japan, 0.15 mg/kg), midazolam (Cat #135-13791, CAS. No 58786-99-5, Wako Pure Chemical Industries Ltd., 2 mg/kg), and butorphanol tartrate (Cat #021-19001, CAS. No 86347-15-1, Wako Pure Chemical Industries Ltd., 2.5 mg/kg), and intraocular pressure was increased unilaterally to approximately 35 mmHg, by intracameral injection of polystyrene microbeads using a single-step, sclero-corneal tunnel approach with a 35G-gauge nanoneedle (# LNAN-3505LM, Saito Medical Instruments Inc., Tokyo, Japan) connected to 100 µl WPI Nanofil 100 microsyringe (World Precision Instruments, Inc., Sarasota, Fla.). Sterile 6 µm polystyrene microbeads in a 1×10⁶ microbeads/ml solution (Molecular Probes, Eugene, Oreg., USA) were concentrated to obtain a 1×10⁷ microbeads/ml solution. This solution was suspended in PBS. The microbeads suspended in PBS were aspirated into a 100 µl Hamilton microsyringe and injected into the anterior chamber of right eye of each animal. 10 µl of the microbead suspension were injected without contacting the cornea or iris with the needle. After stabilization of the elevated IOP, animals were randomly divided into 3 groups (non-treated OHT, AlloP injection, and ent-AlloP injection). AlloP and ent-AlloP were dissolved in 20% w/v (2-Hydroxypropyl)-β-cyclodextrin (2HBCD) in saline solution at concentration of 0.05% (w/v) solution, and injected into the vitreous chamber in a total volume of 1 µl using a Hamilton syringe adapted with a 35G-gauge nanoneedle 1 week after the beads were injected under halothane inhalation anesthesia. OHT animals (vehicle control) received sterile 1 µl 20% (w/v) 2HBCD with PBS. As a further control, 1 µl 20% (w/v) 2HBCD was intravitreally injected 7 days after intracameral injection with 10 µl of PBS. The number of animals used in each experiment is indicated in the corresponding method. The tip of the needle was inserted into the superior hemisphere of the eye at a 45° angle through the sclera into the vitreous body to avoid retinal detachment or injury to eye structures. Ocular hypertension was monitored preoperatively, and at 3 days, 1 week, 2 weeks or 3 weeks after the beads were injected. IOP was measured using a laboratory tonometer (TonoLab, Icare, Finland).

Electron Microscopy—

Retinal specimens were trimmed to a smaller size, and ultrathin sections (75 nm) were cut with a diamond knife and suspended over formvar-coated slot grids (1×2 mm opening). The sections were stained with uranyl acetate and lead citrate and viewed in a transmission electron microscope (H-7650, Hitachi High-Technologies Corp., Tokyo, Japan). Numbers of AP and DAV inside NFLs and axons were determined as the sum in 10 different areas of 25 µm² each from each sample. The analysis was performed in three eyes per experimental condition.

Data Analysis of Morphometry—

The middle portion of the retina was examined, greater than 1,200 µm away from the center of the optic disc along the inner limiting membrane (ILM). The nerve fiber layer thickness (NFLT) was measured by light microscopy along 5 lines perpendicular to the pigment epithelium at a distance of 15 µm from each other around 1,200 µm away from the center of the optic disc. The average NFLT was determined in 9 different light micrographs taken from 5 eyecup samples in each condition, divided by total retinal thickness, and mean±standard deviation (%) was analyzed and compared with control.

The density of degenerated cells characterized by nuclear chromatin clumping or necrosis in the GCL was determined by counting 9 fields of 500 µm length in light micrographs taken from the block of the middle retinal part 950 to 1450 µm away from the center of the optic disc.

The severity of neuronal damage was assessed by light microscopy using a neuronal damage score (NDS). The NDS was determined in 9 different light micrographs taken from 5 eyecup samples in each condition. The NDS rates neuronal damage in the inner nuclear layer (INL) and the inner plexiform layer (IPL) on a 0-4 scale with 0 signifying no neuronal damage and 4 indicating very severe damage. Criteria used in establishing the degree of neuronal damage included the extent of cytoplasmic swelling in the IPL and the number of neurons in the INL showing signs of severe cytoplasmic swelling and coarse clumping of nuclear chromatin. The highest NDS rating (4) is given when the IPL discloses apparent spongiform appearance due to dendritic swelling and when most cell bodies in the INL show severe cytoplasmic swelling and coarse clumping of nuclear chromatin. If the damage is of a lesser degree, a rating of 3 is given. NDS 2 is assigned when cell bodies in the INL are sporadically swollen. In NDS 1, damage does not fulfill higher criteria but the retinas differ from controls (NDS 0). Fine dendritic swelling in a limited area of the IPL without damage in the INL is described by NDS 1.

NFLT, density of degenerated cells in the GCL, and NDS were determined as the measurement of 10 different areas from three eyes per experimental condition. These morphometrical parameters were assessed by three raters, who remained unaware of the experimental condition. Upon completion of data assessment, significance of individual differences among raters was evaluated using five randomly selected samples in each morphometric parameter by one-way analysis of variance (one-way ANOVA) followed by a post-hoc test. There were no significant differences among the raters in any of the morphometric measurements. All data of the NFLT (% vs. retinal thickness), NDS, and the density of degenerated cells in the GCL are expressed as mean±SEM, and evaluated by Dunnett's multiple comparison test compared to controls incubated in aCSF at 10 mmHg or 75 mmHg Preparation of Whole Mounted Retinas and Immunostaining—

The retina was carefully detached from the eye by making cuts along the ora serrata and optic nerve. Whole retinas were then flat-mounted, pinned in an acrylic plate with the RGC layer facing upward using stainless steel pins, and fixed in 4% paraformaldehyde-0.1 M phosphate buffer overnight at 4° C. After the samples were fixed, the tissue was rinsed with PBS three times. To block nonspecific binding, the tissue was incubated in 2% BSA in PBS containing 0.5% Triton X-100. The whole mounted retinas were incubated in the rabbit anti-NeuN polyclonal antibody solution (Cat # ab104225, Abcam, Cambridge, Mass.)) (1:100) by gently shaking at 4° C., overnight. After rinsing 3 times using PBS, the retina was incubated in FITC-conjugated secondary antibody (goat anti-rabbit IgG (H+L)) (Cat #81-6111, Zymed Laboratories Inc., San Francisco, Calif.) (1:300). The retina was then rinsed 3 times with PBS and mounted on glass slides using 50% PBS and 50% glycerol. Retinal flat-mounts were imaged throughout the GCL in each of the four defined retinal quadrants 4 mm from the optic nerve head using a confocal microscope. Each quadrant was analyzed using a 1 mm² frame, and counted using Image-Pro Plus software. The density of NeuN positive RGCs per square millimeter was averaged and compared in experimental retinas treated with 1 µM AlloP or 1 µM ent-AlloP at 75 mmHg and control retinas incubated with aCSF at 75 mmHg by Dunnett's multiple comparison test. RGC counts were analyzed using Image-Pro Plus software. NeuN positive RGCs were determined as the measurement of 5 different areas from three eyes per experimental condition.

Apoptosis—

To visualize apoptotic cells, a DeadEnd™ Colorimetric TUNEL (TdT-mediated dUTP Nick-End Labeling) System (Promega, Madison, Wis.) was used according to the manufacturer's instructions. The nuclei were counterstained with DAPI. After the length of each retinal section was measured (Image-Pro Plus software), the cells were counted in the whole section length and the number of cells was normalized per 200 µm of retinal section. The number of apoptotic cells was evaluated by Dunnett's multiple comparison test to determine changes in the density of apoptotic cells among experimental retinas treated with 1 µM AlloP or 1 µM ent-AlloP at 75 mmHg and control retinas incubated with aCSF at 75 mmHg. Apoptotic cells s were determined as the measurement of 5 different areas from three eyes per experimental condition.

Western Blot Analysis—

At the end of each experiment, the posterior segments of the eye were placed on a flat cutting surface and immersed in ice-cold aCSF. With a surgical blade, the retina was carefully and gently detached from the sclera with a fine forceps. The isolated retinas were frozen at −80° C. Retinas were then homogenized in lysis buffer solution (CelLytic MT; Sigma-Aldrich, Inc.) with protease inhibitor cocktail (Sigma-Aldrich, Inc.), prepared according to the manufacturer's instructions. The tissue extracts were ultrasonicated and clarified by centrifugation at 12,000 g for 20 minutes at 4° C. The protein concentrations in supernatants were assayed (Quant-iT assay kit; Invitrogen Corp., Carlsbad, Calif.). Twenty micrograms of retinal extract were subjected to SDS polyacrylamide gel electrophoretic analysis. The proteins were then transferred to a PVDF. Immunoblots by polyclonal rabbit anti-LC3B antibody (MBL Life Science) or anti-SQSTM1/p62 mouse monoclonal antibody (Abcam) were visualized using WesternBreeze Chemiluminescent Immunodetection system (Invitrogen) with the exposure time to autoradiograph film (MXJB Plus; Kodak, Rochester, N.Y.) adjusted to avoid over- or undersaturation. Precision Plus Protein™ Western Standards (Bio-Rad, Hercules, Calif.) followed by Precision Protein™ strep Tactin-AP conjugate (Bio-Rad) was used for a molecular marker of LC3. MagicMark™ XP Western Protein Standard (Invitrogen, Carlsbad, Calif.) was used for a molecular marker of p62. Immunoblot data are normalized to β-actin levels in the same sample.

The density of Western blot bands was quantified using Image-Pro Plus software. Quantification was adjusted to protein expression at 10 mmHg after normalization to the β-actin band at each pressure, and the relative gray-scale value was calculated by densitometric analysis of the obtained bands. At least four independent experiments were performed for each condition, and the results are presented as relative units numerically. Differences in expression levels were evaluated using Wilcoxon Rank-Sum Test, Tukey's or Dunnett's multiple comparison test. Sample numbers were four to five per each experimental condition.

Chemicals—

AlloP was purchased from Wako Pure Chemical Industries, Ltd. (Cat #596-30841, CAS. NO 516-54-1; Osaka, Japan), and ent-AlloP was synthesized by KK and DFC. 3-MA was purchased from Wako Pure Chemical Industries, Ltd. (CAS. No 5142-23-4, Cat #518-92041). All other chemicals were purchased from Sigma-Aldrich Corp. or Nacalai Tesque (Kyoto, Japan). AlloP and ent-AlloP were dissolved in dimethyl sulfoxide (DMSO) as a 10 mM stock solution.

Statistics—

Data were double-checked and analyzed using a biomedical statistical computer program on a personal computer. Descriptive statistical results were presented using the mean values (mean)±standard deviation (SD). For comparison with controls that were incubated in drug free aCSF at 10 mmHg, Dunnett's multiple comparison test was used, depending on sample numbers. For comparison with both the control and other conditions, Tukey's multiple comparison test was used. For all analyses, p values were considered statistically significant, when the values were less than 0.05 (two-tailed).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that vary depending upon the desired properties sought to be obtained by a particular embodiment. In some embodiments, the numerical parameters are be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) are construed to cover both the singular and the plural, unless specifically noted otherwise. In some embodiments, the term "or" as used herein, including the claims, is used to mean "and/or" unless explicitly indicated to refer to alternatives only or to refer to the alternatives that are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and may also cover other unlisted steps. Similarly, any composition or device that "comprises," "has" or "includes" one or more features is not limited to possessing only those one or more features and may cover other unlisted features.

All methods described herein are performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member is referred to and claimed individually or in any combination with other members of the group or other elements found herein. One or more members of a group are included in, or deleted from, a group for reasons of convenience or patentability. When any such inclusion or deletion occurs, the specification is herein deemed to contain the group as modified thus fulfilling the written description of all Markush groups used in the appended claims.

To facilitate the understanding of the embodiments described herein, a number of terms are defined below. The terms defined herein have meanings as commonly understood by a person of ordinary skill in the areas relevant to the present disclosure. Terms such as "a," "an," and "the" are not intended to refer to only a singular entity, but rather include the general class of which a specific example may be used for illustration. The terminology herein is used to describe specific embodiments of the disclosure, but their usage does not delimit the disclosure, except as outlined in the claims.

All of the compositions and/or methods disclosed and claimed herein may be made and/or executed without undue experimentation in light of the present disclosure. While the compositions and methods of this disclosure have been described in terms of the embodiments included herein, it will be apparent to those of ordinary skill in the art that variations may be applied to the compositions and/or methods and in the steps or in the sequence of steps of the method described herein without departing from the concept, spirit, and scope of the disclosure. All such similar substitutes and modifications apparent to those skilled in the art are deemed to be within the spirit, scope, and concept of the disclosure as defined by the appended claims.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of preventing or treating a neurodegenerative condition comprising inducing autophagy by administering an effective amount of a composition comprising a synthetic enantiomer of a neurosteroid, wherein the neurodegenerative condition is glaucoma and the synthetic entantiomer of the neurosteroid is ent-allopregnanolone.

2. The method of claim 1, wherein the composition further comprises a saline solution.

3. The method of claim 1, wherein administering an effective amount of the composition comprises administering the composition by intravitreal injection.

4. The method of claim 1, wherein administering an effective amount of the composition comprises administering the composition by intracameral injection.

5. The method of claim 1, wherein the synthetic enantiomer of the neurosteroid has a concentration of from about 10 nM to about 100 µM.

6. A method of attenuating pressure- induced retinal injury, the method comprising administering an effective amount of a composition comprising a synthetic enantiomer of a neurosteroid, wherein the injury is glaucoma and the synthetic entantiomer of the neurosteroid is ent-allopregnanolone.

7. The method of claim 6, wherein the composition further comprises a saline solution.

8. The method of claim 6, wherein administering an effective amount of the composition comprises administering the composition by intravitreal injection.

9. The method of claim 6, wherein administering an effective amount of the composition comprises administering the composition by intracameral injection.

10. The method of claim 6, wherein the synthetic enantiomer of the neurosteroid has a concentration of from about 10 nM to about 100 µM.

* * * * *